US009480811B2

(12) United States Patent
Crane

(10) Patent No.: US 9,480,811 B2
(45) Date of Patent: Nov. 1, 2016

(54) SYSTEM FOR MODIFYING A USER'S NEUROLOGICAL STRUCTURE OR NEUROCHEMISTRY BY IMPROVING MOOD, POSITIVITY LEVEL, OR RESILIENCE LEVEL, INCORPORATING A SOCIAL NETWORKING WEBSITE AND METHOD OF USE THEREOF

(71) Applicant: Elizabeth Crane, Elk Grove Village, IL (US)

(72) Inventor: Elizabeth Crane, Elk Grove Village, IL (US)

(73) Assignee: Elizabeth Crane, Elk Grove Village, IL (US)

( * ) Notice: Subject to any disclaimer, the term of this patent is extended or adjusted under 35 U.S.C. 154(b) by 184 days.

(21) Appl. No.: 14/213,748

(22) Filed: Mar. 14, 2014

(65) Prior Publication Data
US 2014/0275740 A1    Sep. 18, 2014

Related U.S. Application Data

(60) Provisional application No. 61/793,238, filed on Mar. 15, 2013.

(51) Int. Cl.
*A61M 21/02* (2006.01)
*A61M 21/00* (2006.01)
*G06F 19/00* (2011.01)

(52) U.S. Cl.
CPC .............. *A61M 21/02* (2013.01); *A61M 21/00* (2013.01); *G06F 19/345* (2013.01); *G06F 19/3481* (2013.01); *A61M 2021/005* (2013.01); *A61M 2021/0027* (2013.01); *A61M 2205/3553* (2013.01); *A61M 2205/3561* (2013.01); *A61M 2205/3584* (2013.01); *A61M 2205/3592* (2013.01); *A61M 2205/505* (2013.01); *A61M 2205/52* (2013.01)

(58) Field of Classification Search
CPC .............. A61M 21/02; A61M 21/00; A61M 2021/0027; A61M 2021/005; A61M 2205/3553; A61M 2205/3561; A61M 2205/3584; A61M 2205/3592; A61M 2205/505; A61M 2205/52; G06F 19/345; G06F 19/3481
See application file for complete search history.

(56) References Cited

U.S. PATENT DOCUMENTS

2010/0037170 A1* 2/2010 Poole .................... G06F 3/0481
                                                    715/772
2012/0315613 A1* 12/2012 Shatte ................... G09B 19/00
                                                    434/236

* cited by examiner

*Primary Examiner* — Christine H Matthews
*Assistant Examiner* — Joshua D Lannu
(74) *Attorney, Agent, or Firm* — Vedder Price P.C.

(57) ABSTRACT

The present invention relates to a software-based system, which may include a social networking website, implemented on a stand-alone computing device or over a network using computing devices. More specifically, the present invention relates to modifying the neurological structure or neurochemistry of a user of the system by improving mood, positivity level, or resilience level either over the Internet or on a stand-alone computing device so as to provide cognitive benefits to the user.

15 Claims, 22 Drawing Sheets

SYSTEM FOR MODIFYING A USER'S NEUROLOGICAL STRUCTURE OR NEUROCHEMISTRY BY IMPROVING MOOD, POSITIVITY LEVEL, OR RESILIENCE LEVEL, INCORPORATING A SOCIAL NETWORKING WEBSITE AND METHOD OF USE THEREOF

CROSS-REFERENCE TO RELATED APPLICATION

The present utility patent application claims priority from and the benefit of U.S. Provisional Patent Application No. 61/793,238, filed Mar. 15, 2013, entitled MOOD ENHANCING SOCIAL MEDIA COMPUTER WEBSITE AND METHOD OF USE THEREOF, the contents of which is hereby incorporated by reference in its entirety.

FIELD OF THE INVENTION

The present invention relates to a software-based system, which may include a social networking website, implemented on a stand-alone computing device or over a network using computing devices for modifying the neurological structure or neurochemistry of a user of the system by improving mood, positivity level, or resilience level either over the Internet or on a stand-alone computing device.

BACKGROUND OF THE INVENTION

A mood is an emotional state that is generally considered to be either positive or negative. Moods typically last longer than emotions and may have less apparent causes. For example, while a person may recognize he or she experiences the emotion of happiness every time he or she sees a loved one, he or she may fail to understand why he or she is constantly anxious. Mood may result from the physical structure of the brain or from the chemical composition of neurotransmitters in the brain. Negative moods may result in significant detrimental effects. Similarly, positive moods may have significant beneficial effects.

All too often, people fail to appreciate the significance that their moods—and thus their mental outlook and emotional states—have on their lives. For example, people assume that they perform equally well regardless of whether they have a positive or negative mood. Even if a person recognizes the impact his or her mood has on his or her performance, the person may fail to recognize the causes of his or her mood or may believe the person has no control over his or her mood.

However, despite these perceptions, research in the fields of neuroscience and positive psychology has demonstrated that people can actually learn to control their moods by training their brains to help them have much happier and more deeply fulfilling lives. In other words, by intentionally creating experiences and performing particular actions, a person may literally change the structure, neurochemistry, and functioning of his or her brain. These changes may be deliberately made in order to improve a person's mood, thereby causing the person to be more positive, resulting in feelings of optimism, happiness and engagement with life.

Furthermore, people often fail to understand the control they can have over their happiness and life satisfaction by enhancing their moods until it is too late. The findings of Bronnie Ware, an Australian palliative care nurse who provides care to patients at the end of their lives, perfectly illustrate this point. She has written a blog about her conversations with these individuals and also turned her writings into a book entitled *The Top Five Regrets of the Dying*. She found that one of the top five regrets that people have at the end of their lives is: "I wish that I had let myself be happier."

Research has demonstrated several ways people may control their moods. For example, research performed by Barbara Fredrickson, Kenan Distinguished Professor of Psychology and principal investigator of the Positive Emotions and Psychophysiology Laboratory (the "PEP Lab") at the University of North Carolina at Chapel Hill indicates that even fleeting positive emotions can tip the scales toward a life of flourishing. Indeed, her research indicates that merely by obtaining a proper ratio (such as three to one) between positive thoughts and negative thoughts, a person can effectively increase their enjoyment of life and better cope with negative events and feelings.

People also may think that the way they deal with stress or negative events is outside their control. However, neuroscientists, such as Richard Davidson at the University of Wisconsin-Madison, have found that individuals who have greater "activation" in their left prefrontal cortex versus their right prefrontal cortex in the brain are more resilient. In other words, people with this higher activation will bounce back more quickly from setbacks. His research indicates that people with greater activation on the left side of the prefrontal cortex recovered much more quickly from even the strongest feelings of disgust, anger, and fear. Further, his research indicates that by intentionally cultivating experiences that create activation of the left prefrontal cortex, a person can cause himself or herself to be more resilient.

A person's mental outlook has a direct impact upon their cognitive performance. Shawn Achor, a former professor at Harvard University and author of the book, *The Happiness Advantage*, shows in his research that when people are in "a positive brain" they are thirty-one percent more productive and three times more creative. For example, if a person in a positive brain works in sales, he or she will sell thirty-seven percent more that someone who is not. Similarly, if such a person is a physician, he or she will diagnose nineteen percent more quickly and accurately than if he or she is in "a negative, neutral or stressed brain."

Research indicates that a number of health benefits come from positive moods. For example, by enhancing their moods, people may live longer, decrease their stress levels, decrease their likelihood of suffering from physical disease, decrease their likelihood of suffering from depression, and generally increase their physical well-being. Additionally, enhancing their mood may help relieve symptoms of mood disorders, such as, for example, clinical depression and bipolar disorder.

A blog article entitled, *How Positive Thinking Re-Wires Your Brain* by Barrie Davenport discusses the book, *The Brain That Changes Itself: Stories of Personal Triumph from the Frontiers of Brain Science*, by Norman Doidge M.D. In this article, Barrie Davenport states that Dr. Doidge's work shows that the brain has the capacity to rewire itself and/or form new neural pathway if we do the work. Just like exercise, the work requires repetition and activity to reinforce new learning.

Accordingly, a need exists for a system for enabling people to "rewire" their brains in order to obtain cognitive benefits associated with positive moods, such as greater happiness, enjoyment of life, resilience in coping with negative events, and increased productivity and creativity.

SUMMARY OF THE INVENTION

An embodiment of the present invention provides a system for promoting and encouraging positive thinking and behavior in order to provide cognitive benefits to a user of the system by altering the neurochemistry and neurological structure of the user, the system comprising a processor, a memory, a display, and an input device, the memory operating a program executing the steps of:

presenting the user with a user interface providing at least one task associated with positive behavior via the display;

adapting the user interface based on an input from the user to allow the user to complete one or more of the at least one task associated with positive behavior via the input device;

determining whether the user completed one or more of the at least one task associated with positive behavior;

tracking the number of tasks associated with positive behavior completed by the user;

displaying, with the user interface via the display, a first indicium representing the number of tasks associated with positive behavior completed by the user;

adapting the user interface to present the user with at least one action via the display, wherein the at least one action is determined based in part on the number of tasks associated with positive behavior completed by the user;

measuring at least one attribute of the user, wherein the attribute is selected from the group comprising a mood, a positivity level, and a resilience level, at a plurality of times using one or more of a plurality of tests, wherein the one or more of the plurality of tests are displayed to the user via the display device and require the user to provide an input using the input device;

tracking the at least one attribute of the user at the plurality of times by recording the results of the one or more of the plurality of tests;

displaying, with the user interface via the display, a second indicium representing the at least one attribute of the user at the plurality of times;

alerting the user via the display to one or more of a plurality of factors that may affect the at least one attribute of the user based on the results of the one or more of the plurality of tests;

modifying the user's neurological structure or neurochemistry by improving the at least one attribute of the user so as to provide cognitive benefits to the user.

An embodiment of the present invention provides a system for promoting and encouraging positive thinking and behavior in order to provide cognitive benefits to a user of the system by altering the neurochemistry or neurological structure of a user of the system, comprising:

at least a host computer comprising a central processing unit (CPU) for executing a software; a memory communicatively connected to the CPU for storing the software; a display device communicatively connected to the CPU, and an input device communicatively coupled to the CPU, wherein the software comprises:

a task generation module that generates a plurality of tasks designed to alter the neurochemistry or neurological structure of the user, displays the plurality of tasks to the user via the display device, receives a first input from the user via the input device indicating at least one selected task from the plurality of tasks, and allows the user to complete the at least one selected task via the display device and the input device;

a progress recordation module that records the progress of the user in completing the plurality of tasks and displays the progress of the user in completing the plurality of tasks to the user via the display device;

a reward module that generates a plurality of actions, displays the plurality of actions to the user via the display device, receives a second input from the user via the input device indicating at least one selected action from the plurality of actions, and allows the user to perform the at least one selected action via the display device and the input device, wherein the plurality of actions is determined based on the progress of the user in completing the plurality of tasks;

a measurement module that measures at least one attribute of the user, wherein the attribute is selected from the group comprising a mood, a positivity level, and a resilience level, displays a plurality of tests to the user via the display device, receives a third input from the user via the input device indicating at least one selected test from the plurality of tests, and administers the at least one selected test to the user via the display device and the input device;

a recordation module that records the at least one attribute of the user based on the results of the at least one selected test and displays an indication of the at least one attribute of the user to the user via the display device; and a recommendation module that generates at least one recommendation for the user and displays the at least one recommendation to the user via the display device, wherein the at least one recommendation is based at least in part on the at least one attribute of the user, lists at least one factor that may affect the at least one attribute of the user, and is designed to assist the user in positively altering the user's neurochemistry or neurological structure.

An embodiment of the present invention provides a method for promoting and encouraging positive thinking and behavior in order to provide cognitive benefits to a person using a social network by altering the person's neurochemistry or neurological structure, comprising:

determining a plurality of tasks to be performed using the social network designed to positively alter the person's neurochemistry or neurological structure;

instructing the person to perform a selected one or more of the plurality of tasks using the social network;

monitoring the progress of the person in completing the selected one or more of the plurality of tasks on the social network;

informing the person of their progress in completing the selected one or more of the plurality of tasks;

measuring at least one attribute of the person, wherein the attribute is selected from the group comprising a mood, a positivity level, and a resilience level, by providing the person with one or more quizzes using the social network;

recording the at least one attribute of the person based on the results of the one or more quizzes;

informing the person of the at least one attribute of the person; and recommending, based on the at least one attribute of the person, at least one action the person may take to mitigate the effects of at least one factor that is harmfully impacting the person's neurochemistry or neurological structure.

BRIEF DESCRIPTION OF THE DRAWINGS

Certain embodiments are shown in the drawings. However, it is understood that the present disclosure is not limited to the arrangements and instrumentality shown in the attached drawings.

DETAILED DESCRIPTION

Figure 1:
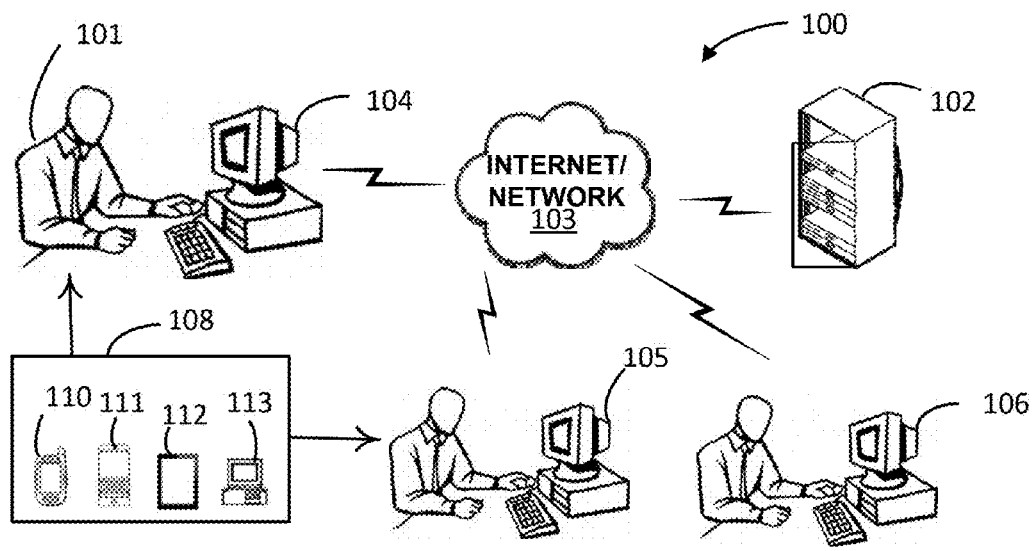
FIG. 1 is an illustration of a hardware system wherein a system and method in accordance with the present invention can be implemented.

For the purposes of promoting and understanding the principles disclosed herein, reference is now made to the preferred embodiments illustrated in the drawings, and specific language is used to describe the same. It is nevertheless understood that no limitation of the scope of the invention is hereby intended. Such alterations and further modifications in the illustrated devices and such further applications of the principles disclosed and illustrated herein are contemplated as would normally occur to one skilled in the art to which this disclosure relates.

Described herein are embodiments of systems and methods for enabling people to improve their moods and improve their cognitive functioning. These systems may be implemented using a variety of hardware and may interact with users in order to improve their moods and affect their cognitive functioning. Software operates as a set of instructions running in executable memory of a processor residing on a computing device. To fully enable the software and its functionality described herein, the present disclosure begins with a summary of how computers may be used, either alone or in a networked configuration.

Hardware

FIG. 1 illustrates a hardware configuration 100 wherein a system can be implemented on one or more computers 104, 105, and 106 used by different users 101 and connected over a network 103. The network 103 is suitable for connecting the one or more computers 104, 105, and 106 and may comprise one or more networks such as a local area network (LAN), a wide area network (WAN) such as the Internet, telephone networks including telephone networks with dedicated communication links and/or wireless links, and wireless networks. In the illustrative example shown in FIG. 1, the network 103 is the Internet. Each of the one or more computers 104, 105, and 106 is connected to the network 103 via a suitable communication link, such as a dedicated communication line or a wireless communication link. The system may be implemented using software that is either local or operating from a remote server 102 such as a web server over the Internet. Further, with the rapid growth of Internet technology and portable wireless technology, other computing devices, such as but not limited to, cell phones 110, handheld devices 111, different portable tablets 112, or portable computers 113 may be used place of or in addition to the one or more computers 104, 105, and 106.

Each of the one or more computers 104, 105, and 106 comprises a central processing unit (CPU), an input/output (I/O) unit, a display device communicatively coupled to the I/O unit, a storage device, and a memory. Each of the one or more computers 104, 105, and 106 may further comprise one or more standard input devices such as a keyboard, a mouse, speech processing means, or a touchscreen. The memory includes a Graphical User Interface (GUI) that is used to convey information to and receive information from a user of the one or more computers 104, 105, and 106 via the display device and I/O unit as described herein. The GUI includes any user interface capable of being displayed on a display device including, but not limited to, a web page, a display panel in an executable program, or any other interface capable of being displayed on the one or more computers' 104, 105, and 106 respective display device.

As will be recognized by one of skill in the art, each of the cell phones 110, handheld devices 111, different portable tablets 112, or computers 113 may be configured similarly to the one or more computers 104, 105, and 106, taking into account the various design considerations of these respective devices.

The GUI may be transmitted to the one or more computers 104, 105, and 106 or other devices 110, 111, 112, or 113 via the network 103. In one embodiment in accordance with the present invention, the GUI is displayed using commercially available hypertext markup language ("HTML") viewing software such as, but not limited to, Microsoft Internet Explorer, Google Chrome, Apple Safari, or Mozilla Firefox, or any other commercially available HTML viewing software.

The GUI may reside on a remote server 102. The remote server 102 may comprise one or more separate servers. The remote server 102 may be a web server. The remote server 102 may comprise a CPU, memory, and separate storage device and be communicatively coupled to the network 103. The remote server 102 may contain an information storage device that may be a rational database, such as Microsoft's SQL or any other database.

It's All Good Here™

In an embodiment of the present invention, the system includes a website in the form of a social network called It's All Good Here™ (IAGH). This website functions to improve users' moods, spread positivity and happiness throughout the world, uplift people, and help users to mentally master life's daily difficulties while giving them a powerful mental edge in life and in work. To accomplish this, the IAGH website helps "wire" users' brains for positivity, by improving users' moods, and positivity and resilience levels, thereby changing the structure, neurochemistry, and functionality of a users' brains.

In an embodiment of the present invention, one social network and resource exists for the public along with a separate platform for companies to use internally to improve employee morale, engagement, camaraderie, resilience, and productivity. In an embodiment of the present invention, the system spreads positivity and happiness throughout the world by providing a boost to users' morale. The system uplifts people's spirits by providing an increased sense of camaraderie. The system helps users mentally master life's daily difficulties by helping them to increase their resilience. The system gives users a powerful mental edge in life and in work by improving their cognitive performance, resulting in better productivity and creativity. The system leverages proven techniques, such as repetition, to assist users in reprogramming their brains to achieve desired results, such as making a user happier and more resilient. The system leverages the concept that a brain becomes wired to more easily perform actions on which an individual focuses. For example, by focusing on things that make an individual happy, the individual can reconfigure his or her brain to be happy more often. Similarly, by focusing on positive things, a person's brain will increase in positivity. Accordingly, by focusing on positive things, a person can train their brain to be more positive.

Neuroplasticity refers to the manner in which the structure and functioning of the brain may be changed. These changes in structure may be caused by disease or serious health events, such as strokes. However, recent research has demonstrated that the structure and functionality of the brain can be changed simply by repeatedly performing an action or thinking a thought. A simple example of this phenomenon is how repeated exposure, for example through flash cards, enables a person to easily recall long lists of words in a foreign language and their definitions. By repeatedly exposing a brain to positive thoughts or messages, a person can change the structure of their brain so as to cause them to experience more positivity or happiness. As this repetition occurs, the brain physically changes its structure by creating new neural connections. Just as exercises allow muscles to grow stronger, exercises can allow a brain to become stronger and better able to cope with negative events. Conversely, if a person allows himself or herself to dwell on negative thoughts, his or her brain will become wired to think negatively. Accordingly, a system in accordance with an embodiment of the present invention uses repetition of positive or desirable messages and avoidance of negative or unwanted messages to increase the positivity and happiness of a person's brain.

In an embodiment in accordance with the present invention, the IAGH website includes several pages, each with one or more distinct purposes. A website in accordance with the present invention may comprise one or more of the following sections for a user to uplift himself or herself or his or her family, friends or colleagues, each of which may comprise multiple pages: a loading page, a main page, a score card, a fun center, journals, mood flippers, relief street, and favorite things. Each of these sections is discussed in detail in turn. Additional sections, such as, for example, a section titled dump the junk, may also be included. It should be understood that the system and methods described herein for enhancing mood may be applied in various ways such as, for example, through social networking websites, other websites, or dedicated applications.

Loading Page

Figure 2:
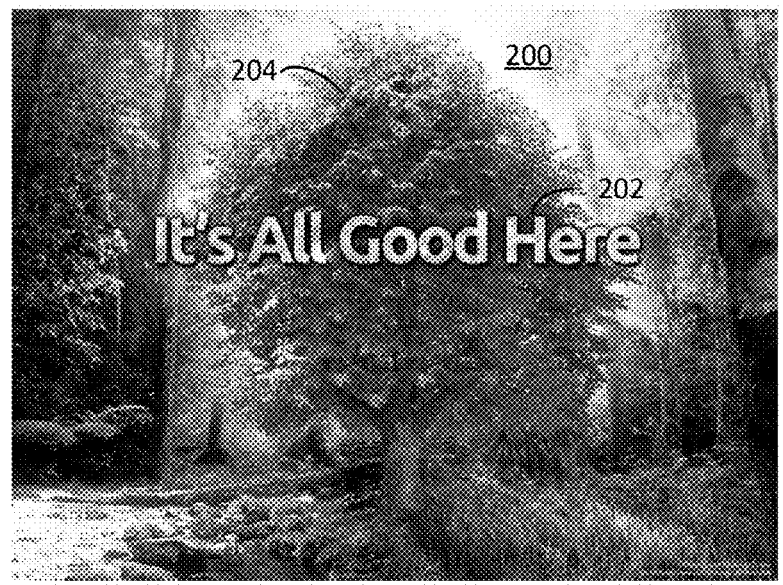
FIG. 2 is an illustrative embodiment of a loading page of a social networking website.

As shown in the illustrative embodiment depicted in FIG. 2, a system in accordance with an embodiment of the present invention may include a website that presents a user with a GUI comprising a loading page 200 that includes the name of website 202. The loading page 200 may feature an image 204 designed to relax the user and promote feelings of calmness and happiness. For example, as depicted in FIG. 2, the loading page 200 may include a peaceful image of nature, such as a tree standing in the middle of a sunlit clearing in a forest next to a stream. The loading page 200 may be the first page displayed to a user upon accessing the website. This loading page 200 may, for example, serve to prime a user to rewire his or her brain by suppressing chaotic or negative thoughts from the moment the user visits the website.

Main Page

Figure 3:
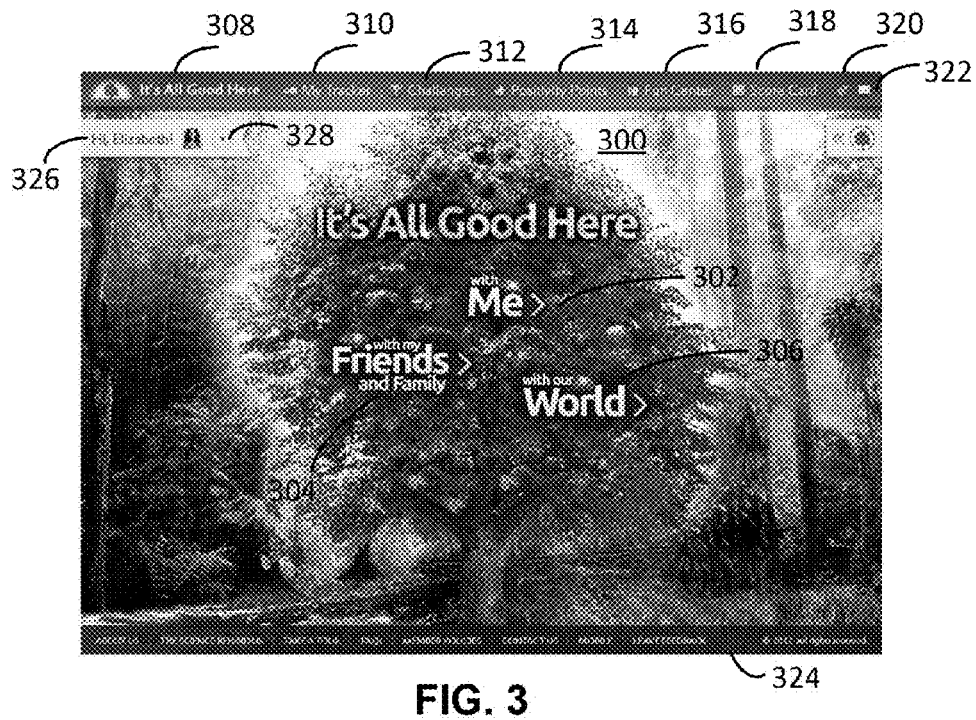
FIG. 3 is an illustrative embodiment of a main page of a social networking website.

With reference to FIG. 3, an illustrative embodiment of a main page for use by the public is shown. As shown in FIG. 3, the GUI may present the user with a main page 300. In an embodiment, the main page is displayed to a user after the loading page, once the website has been copied into the local memory of the user's computer. The main page 300 may be divided into three major segments: With Me 302, With My Friends and Family 304, and With Our World 306. The three segments 302, 304, and 306 work to uplift people in their relationships with themselves, with their friends, and with the world at large, respectively. As will be understood by one of skill in the art, other segments may be used in addition to or in place of the three segments 302, 304, and 306. For example, in an embodiment, the main page 300 may be divided into two major segments, such as Uplift Yourself and Uplift Others.

A menu bar 308 at the top of the main page 300 contains buttons linking to other pages on the website including My Tracker 310, Challenges 312, Positivity Points 314, Fun Center 318, and Score Card 318. Each button may comprise text and an icon. These other pages are discussed individually below. Additional buttons, such as one for settings 320 or messages 322, may also be included in the menu bar 308. A footer 324 may be located at the bottom of the main page 300. The footer 324 may contain additional links to pages describing IAGH, providing help or further explanation regarding the use of the website, providing policy information applicable to users of the website, providing contact information for the administrators of the website, or offering additional versions of the website, such as a mobile version.

As will be clear to one of skill in the art, the menu bar 308 and footer 324 may optionally be repeated on additional web pages aside from the main page 300 to aid users in efficiently navigating the website.

Score Card

The Score Card section tracks a user's progress in controlling his or her mood and rewiring his or her brain. The Score Card section may comprise a Positivity Points page, a Personal Payout page, and a Progress page (also referred to as the Mental Edge/Black Belt page). Each page is discussed in turn.

Figure 4:
FIG. 4 is an illustrative embodiment of a Positivity Points page of a social networking website.

Referring to FIG. 4, an illustrative example of the Positivity Points page 400 is shown. The Positivity Points page 400 may be reached, for example, by clicking the Positivity Points link 314 in the menu bar 308.

As shown in FIG. 4, according to an embodiment of the invention, for every single action a user takes on the website, the user receives one or more Positivity Points. A Positivity Point is a reward given to a user for accomplishing something positive. Users are thereby motivated to take positive actions in order to gain Positivity Points. The Positivity Points page 400 displays a summary 402 of the categories of actions taken by the user and the number of Positivity Points received for these actions. The summary 402 may include the number of Positivity Points earned using each of the main features on the website. In the illustrative example shown in FIG. 4, totals for three of the main features are individually displayed. These three main features are uplifting messages received 402a, uplifting messages sent 402b, and Mood Flippers completed 402c. Additionally, a combined total for all other actions completed 402d is shown. A user may obtain additional information about the other actions that have earned Positivity Points by selecting the other actions completed 402d section.

The Positivity Points page 400 also includes a Positivity Print 404. The Positivity Print may be located next to the summary 402. The Positivity Print 404 is a symbol of the positive things a user has done as well as a reflection of the total number of Positivity Points that the user has earned. The Positivity Print 404 has different levels based on the number of Positivity Points a user has earned. Each level unlocks new rewards for the user. For example, when a user has earned one hundred Positivity Points, the user will reach the one hundred point level on the Positivity Print 404 and will unlock gifts in the Fun Center at the one hundred point level. As is discussed below, a user can then send these gifts to his or her friends. In this way, the more positive actions a user performs, the more Positivity Points the user receives, thereby unlocking successively higher levels of gifts at the Fun Center and enabling the user to take additional positive actions. Each level the user advances to in the Fun Center has more advanced and sophisticated gifts. Users are thereby inspired to want to do more positive things in order to gain additional Positivity Points. Doing these positive things serves to alter the structure, neurochemistry, and function of the users' brains, thereby enhancing their moods and conferring additional benefits as discussed herein.

This cycle of positive actions earning rewards that enable the user to perform further positive actions helps rewire the user's brain. By repeatedly performing positive actions, the user becomes accustomed to performing positive actions and begins to form a habit whereby the user seeks to continue to perform positive actions without further prompting.

In an embodiment, a calendar 406 is located on the Positivity Points page 400. The calendar 406 may be located under the summary 402 of Positivity Points and the Positivity Print 404. The calendar 406 displays the number of Positivity Points a user earned each day. The calendar 406 may display points earned on a daily, weekly, monthly or yearly basis.

Referring again to FIG. 3, a tab 326 located on the side of the main page 300 may display the user's name and profile picture along with a miniature version 328 of the Positivity Print 404. This miniature version 328 allows a user to quickly determine when the user has advanced in level. The system allows a user to elect to display this miniature version 328 to other users of the website, in order to show his or her progress in gaining Positivity Points. Additionally, users may publish their Positive Print 404 or its miniature version 328 on other, third-party websites such as, for example, social networking websites such as Facebook® or Google+®.

Figure 5:
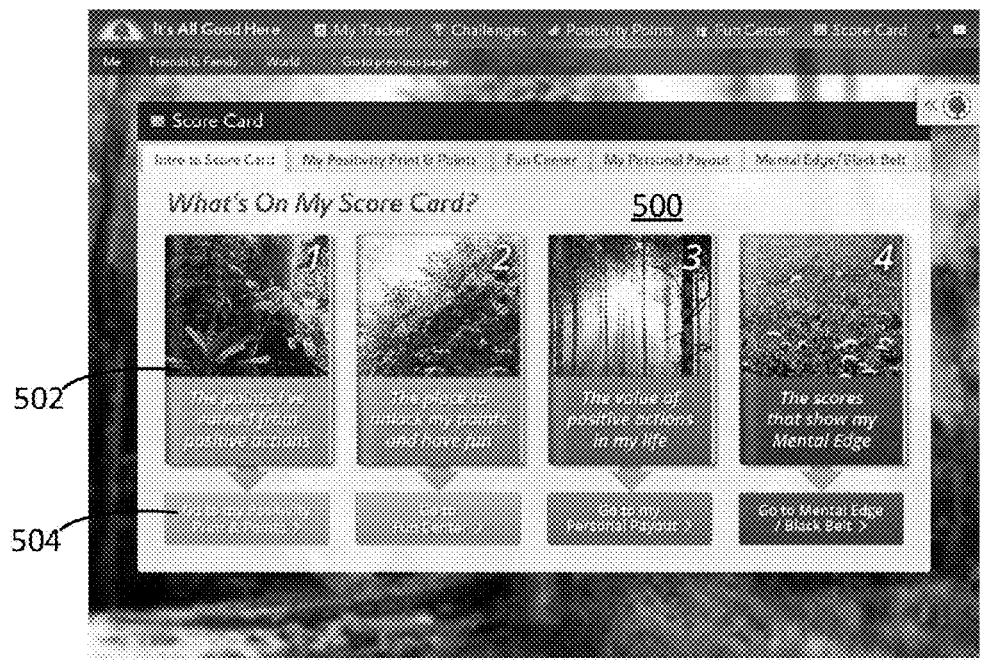
FIG. 5 is an illustrative embodiment of an introductory page of a social networking website.

Referring now to FIG. 5, an illustrative example of an introduction page 500 is shown. The introduction page 500 may display information 502 explaining the functionality of the website, including, for example, the Positivity Points page 400. The introduction page 500 may also contain buttons 504 linking to the various subsections of the Score Card.

Figure 6:
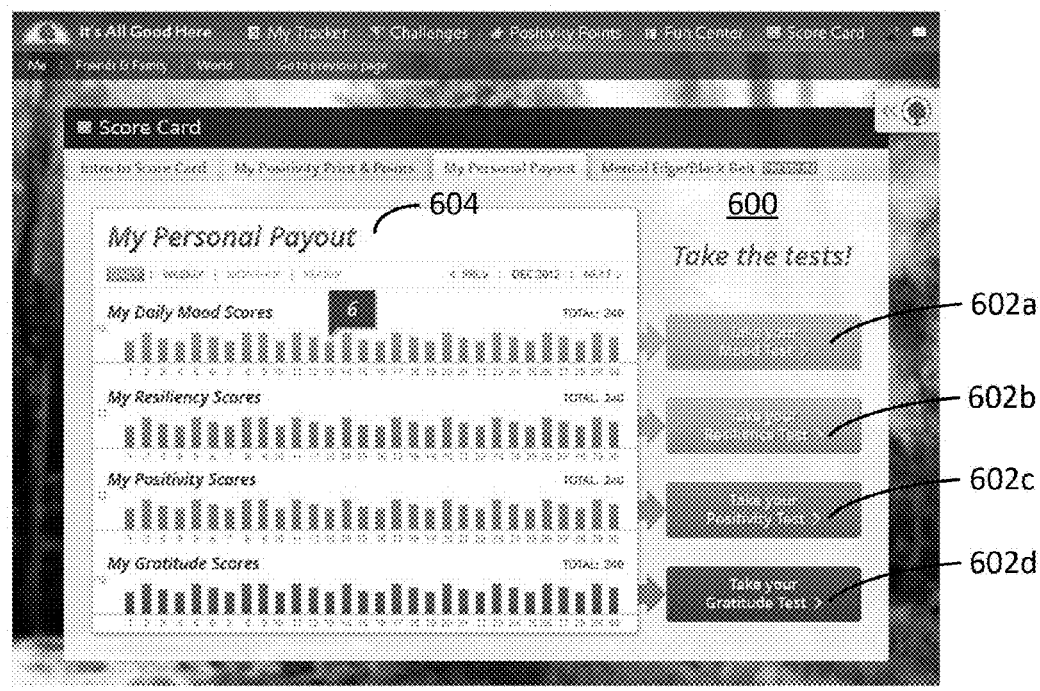
FIG. 6 is an illustrative embodiment of a My Personal Payout page of a social networking website.

Referring to FIG. 6, an illustrative example of the My Personal Payout page 600 is shown. The My Personal Payout page 600 may include a number of quizzes 602a-602d or questionnaires that a user may select in order to test the user's daily mood, resiliency, positivity and gratitude levels. A summary 604 of the user's scores on the quizzes 602 a-602d may also be displayed. As shown in FIG. 6, the quizzes may include, for example, a test for mood 602a, a test for resilience 602b, a test for positivity 602c, and a test for gratitude 602d. Additional quizzes 602 or different combinations of quizzes 602 may also be used.

As a user performs actions on the website, the user's scores on the quizzes 602 a-602d will improve. This occurs because the user is rewiring the user's brain, making the user happier, more resilient, more positive, and more grateful. The summary 604 displays the user's scores on the quizzes 602 on a daily, weekly, monthly and yearly basis.

A user may take quizzes every day, thereby measuring both daily changes and allowing for overall trends to be observed. For example, a user may use a quiz 602 to rate the user's mood on a scale of one to seven every day. Frequent measurements, such as daily measurements, allow the system to determine trends in the user's mood. For example, a user who is in a good mood only on the weekend may be dissatisfied with the user's job during the week. By observing trends, the system may alert the user to sources of negative moods and provide suggestions for addressing these negative moods.

A variety of different quizzes may be used. For example, in an embodiment, a test for positivity 602c is used such as the Positivity Ratio Test developed by Barbara Fredrickson, Kenan Distinguished Professor of Psychology at the University of North Carolina at Chapel Hill. Similarly, in an embodiment, a test for resiliency 602b is used such as the Resilience Test, which was developed by Professor Richard Davidson at the University of Wisconsin-Madison.

Figure 7:
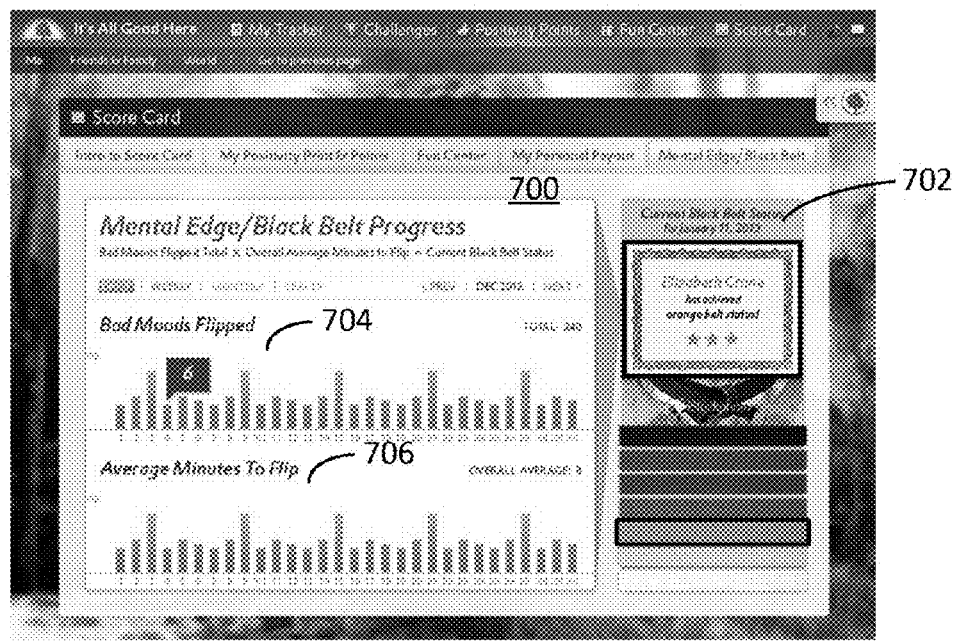
FIG. 7 is an illustrative embodiment of a progress page of a social networking website.

Referring to FIG. 7, in an embodiment the system includes a Progress page 700. A user may receive status indicators representing the user's progress in controlling his or her moods. These status indicators may be, for example, colored belts. A user may be awarded a colored belt based on several factors. The Progress page 700 may display the highest level of belt awarded to a user 702. In the illustrative embodiment shown in FIG. 7, one factor used in determining a user's progress is the number of times the user has performed actions on the website that caused the user to flip from a negative mood to a positive mood. The user's progress is recorded as the number of negative moods flipped 704 by the user. Similarly, another factor is the amount of time required for the user to flip the user's mood. The user's progress is shown as the average time 706 required for the user to flip the user's mood, for example measured in minutes.

For example, in an embodiment a user tracks the user's mood on a scale of one to seven on a real-time basis using quizzes 602 on the website. As the user performs actions on the website to improve the user's mood, the user records the change in their mood by entering the user's new mood score. The user will be awarded a colored belt depending on the number at which the user's mood started, the number to which the user raised the user's mood, and how long it took the user to perform the increase. For example, in an embodiment, increasing a mood score to six will signify that a user has flipped from a negative or bad mood to a positive or good mood. This may be termed a "Flipped Mood."

These colored belts may be termed Mental Edge Belts and may range in color from White to Black, with Black being the highest level. These Mental Edge Belts reflect the mental mastery, or control, a person has over the person's mood. In other words, the Mental Edge Belts serve as an indicator to users of their progress in controlling their moods.

On the Progress page 700, a user may view the user's number of Flipped Moods and the time required to perform a Flipped Mood on a daily, weekly, monthly, or yearly basis. Similarly, the Progress page 700 may include a section displaying a user's average belt level history on a daily, weekly, monthly or yearly basis. The progress page 700 may display a user's most current belt level 702, for example, on the right side of the page.

Fun Center

In an embodiment in accordance with the present invention, the system includes a "Fun Center" section including three subsections: "Create Gifts"; "Gifts I've Sent"; and "Gifts I've Received." In the first subsection, a user may create a gift to send to a friend. In the second subsection, a user may view all of the gifts they have sent. In the third subsection, a user may view all of the gifts they have received.

Figure 8:
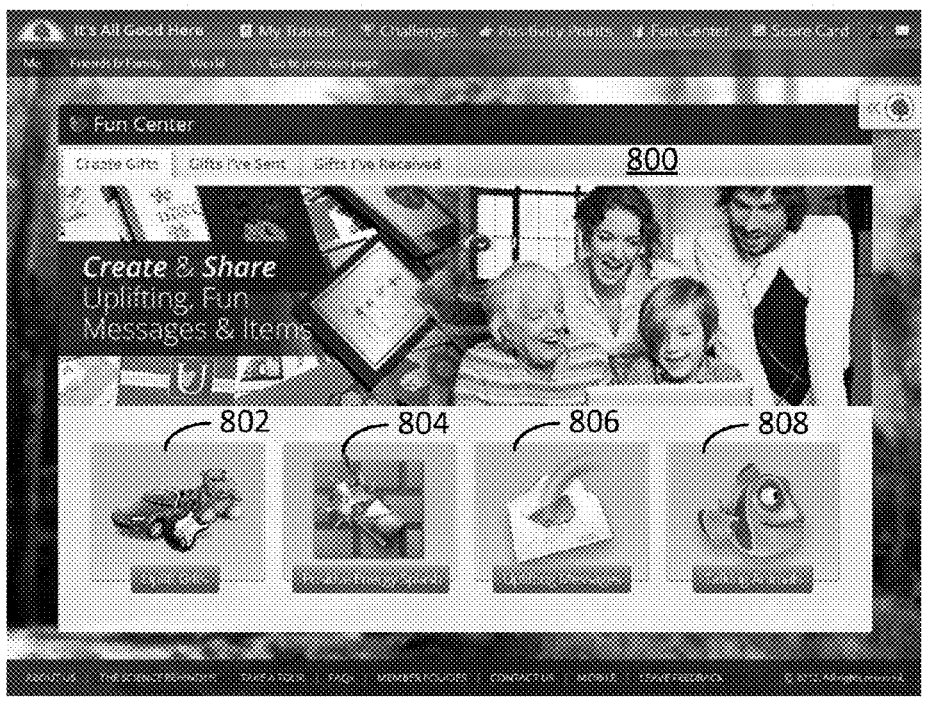
FIG. 8 is an illustrative embodiment of a Fun Center page of a social networking website.

With respect to FIG. 8, an illustrative embodiment of a Fun Center page 800 in the first subsection for creating a gift is shown. In the embodiment shown in FIG. 8, there are four main sections on the Fun Center page 800: Uplift Gifts 802; Positive Energy Splashes 804; Uplifting Messages 806; and Talking Animals 808 (also referred to as Creative Critters). Each of these sections represents a different category of gifts or uplifting messages that a user can send to his or her friends using the Positivity Points the user has earned.

Figure 9:
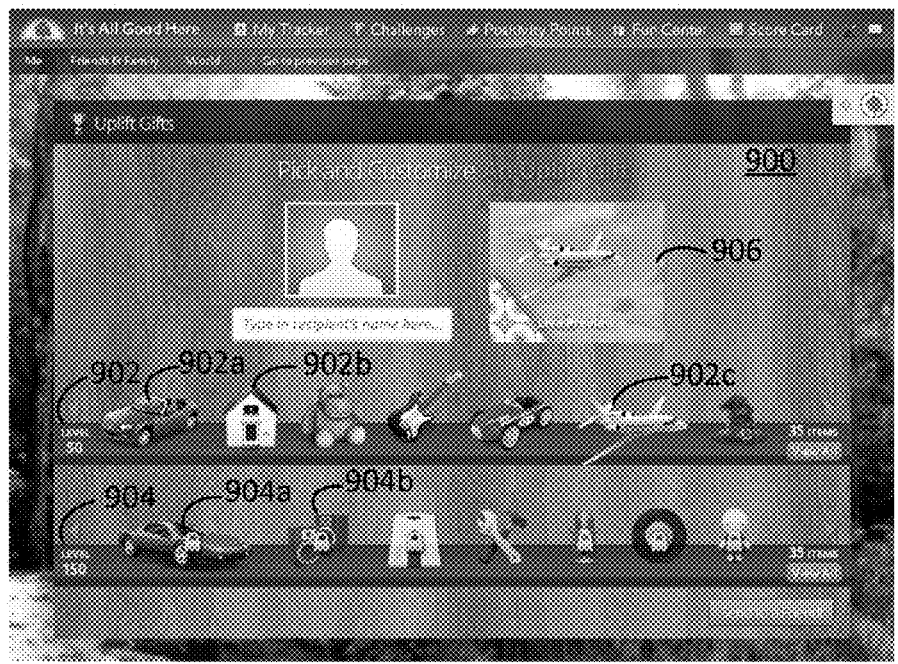
FIG. 9 is an illustrative embodiment of a page for sending an Uplift Gift on a social networking website.

With respect to FIG. 9, an illustrative embodiment of a page 900 for sending a gift from the first category, Uplift Gifts, is shown. The page 900 may contain one or more rows 902, 904 each containing one or more gifts such as gifts 902a, 902b, 902c, 904a, 904b. In the illustrative example shown in FIG. 9, a user who has reached level fifty has access to all of the gifts in the first row 902, such as gift 902a, gift 902b, and gift 902c. However, the user may not access the gifts on the second row 904, such as gift 904a and gift 904b. This may be shown by placing a lock icon over each of the gifts 904a, 904b in the second row 904. To access the gifts on the second row 904, the user must first reach level one hundred fifty.

A user may select one of the unlocked gifts to send to a friend. In the illustrative example shown in FIG. 9, the user may, for example, select a gift 902c. An image of the selected gift 902c then appears in the live preview box 906. The live preview box 906 may be located on the upper right side of the page 900.

In an embodiment, a color palette is displayed, enabling the user to select a color for the gift 902c. The colors available depend on the user's level, with higher levels enabling the user to choose from more desirable colors. For example, a user at the fifty-point level might have the option to choose from five basic colors, while a user at the one thousand-point level has the option to choose from many glittery exotic colors. A user may select one or more of the available colors to apply to the gift 902c, thereby changing the color of the gift 902c displayed in the live preview box 906.

After selecting and customizing a gift, the user may then send the gift to one or more of the user's friends. In an embodiment, the user may choose virtual wrapping paper to use for the gift. As discussed above, high-level users may have a greater number of options, and more desirable options, to choose from. After a gift is sent, an image of the virtual gift appears in the recipient's inbox and the recipient is notified that he or she has received an Uplift Gift.

Figure 10:
FIG. 10 is an illustrative embodiment of a page displaying a Positive Energy Splash gift on a social networking website.

With respect to FIGS. 10-13, an illustrative embodiment of a section for creating a gift from the second category, Positive Energy Splash, is shown. As shown in FIG. 10, a page 1000 shows a completed a Positive Energy Splash gift. This gift allows users to send "Positive Energy" in the form of a virtual paint splash to their friends. On the page 1000, a virtual canvas 1002 is covered with virtual paint 1004. Each splash of virtual paint 1004 will go on the virtual canvas 1002. Paint 1004 may be applied by a plurality of a user's friends to a single canvas 1004, with each user applying one or more separate splashes, together creating a combined painting for the user. As a user's friends fill up the user's canvas 1002 by sending positive energy paint splashes 1004 to the user, a secret message 1006 is revealed letter by letter as the paint 1004 splashes on the canvas 1002. For example, the secret message 1006 could be "You Are the Best" or "You Mean the World to Me". As shown in FIG. 10, when the canvas 1002 is completely covered, entire message 1006 is revealed.

Figure 11:
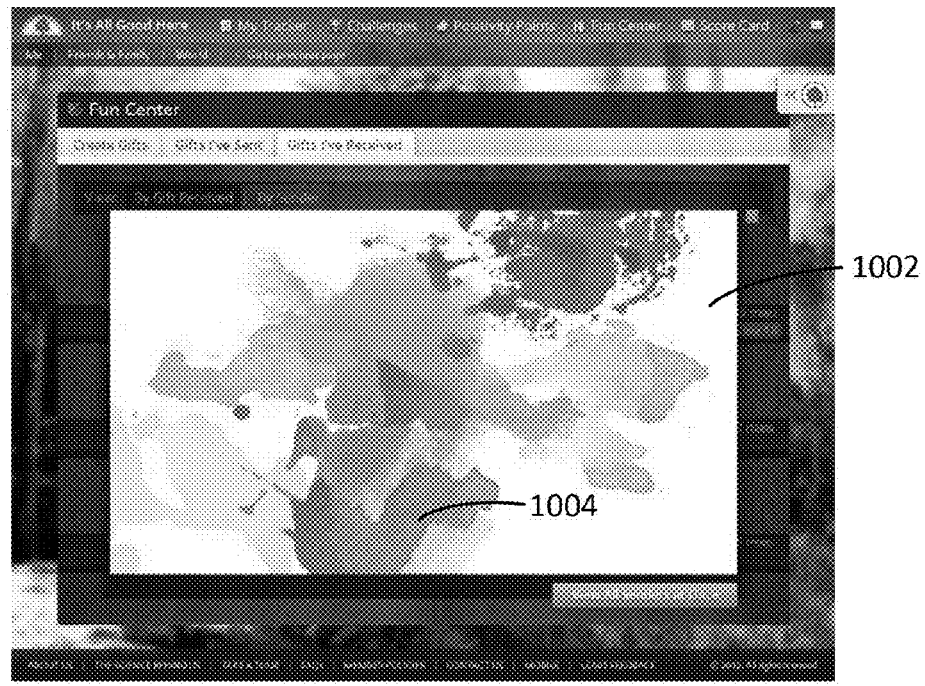
FIG. 11 is an illustrative embodiment of the hidden message being revealed in a Positive Energy Splash.

As shown in FIG. 11, the message 1006 is not visible until sufficient paint 1004 is applied to the canvas 1002.

Figure 12:
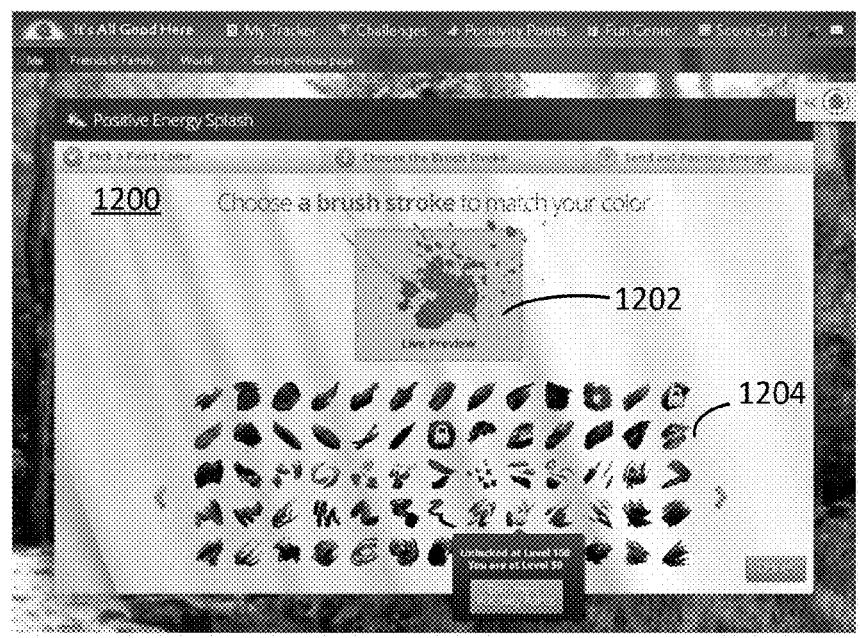
FIGS. 12-13 are illustrative embodiments of different options available for creating a Positive Energy Splash.
Figure 13:
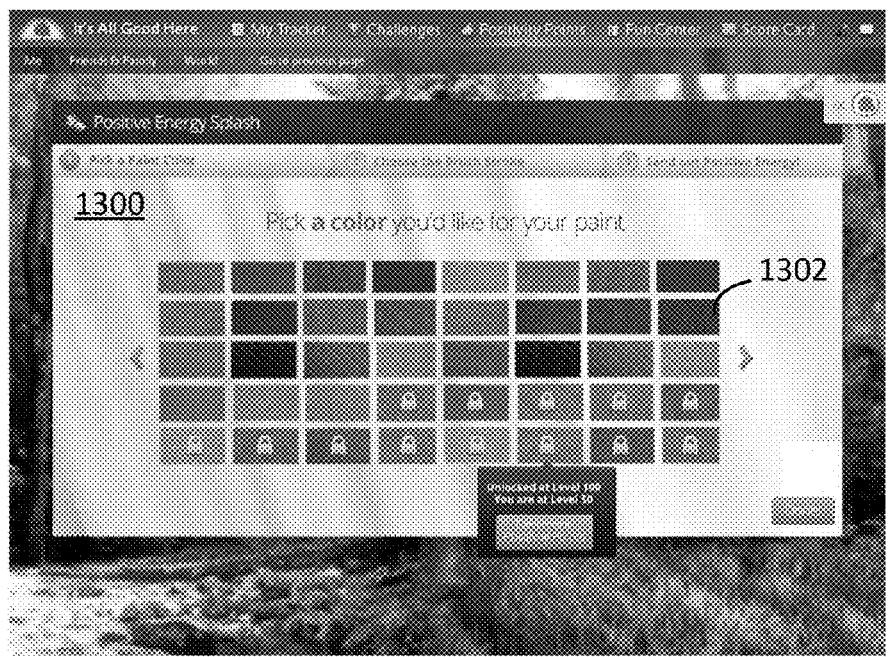

As shown in FIGS. 12 and 13, the more Positivity Points that a user has earned, the more colors of paints and options of brush strokes are available. For example, paints at the one-hundred level may be primary colors, paints at the five-hundred level may be multicolored, paints at the one-thousand level may have glitter in them, and paints at the two-thousand level may be color-changing. In the illustrative embodiment shown in FIG. 12, a page 1200 contains a preview box 1202 and a number of options of brush style 1204. After a user has selected a color, the user may select a brush style 1204. The selected combination of color and brush style will appear in the preview box 1202. In the illustrative embodiment shown in FIG. 13, a page 1300 contains a number of options of paint colors 1302 for a user to select.

For the third category of gifts, Uplifting Messages, a page (not shown) allows a user to enter the text of a message into a first text box and the name of one of the user's friends into a second text box. The user may then send the message to the user's friend. In an embodiment, an option is provided to allow the user to select one or more visual depictions of emotion, such as emoticons, or other images to accompany the message. As discussed above, a higher-level user may have a greater number of desirable options to select for the images to accompany the message.

Figure 14:
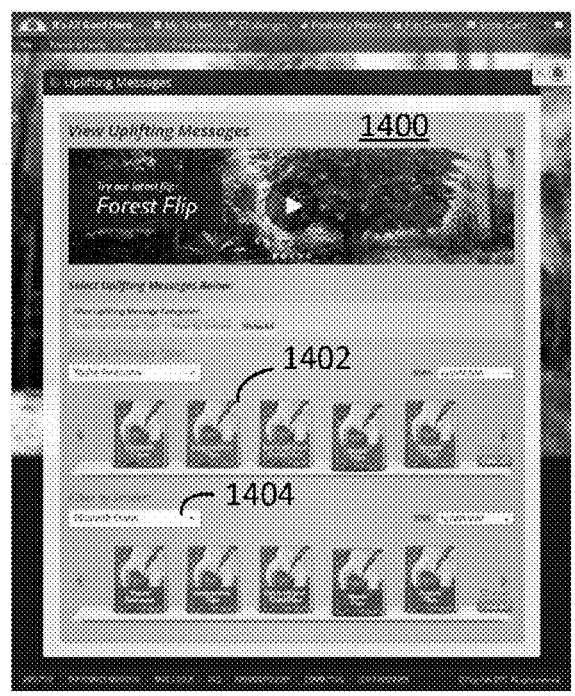
FIG. 14 is an illustrative embodiment of a page containing a record of messages sent to a user of a social networking website.

As shown in the illustrative embodiment depicted in FIG. 14, a user's Uplifting Messages page 1400 includes a record of all of the uplifting messages 1402 a user has received. These messages 1402 may be sorted into categories 1404, such as by message type or by sender. When a user is having a hard day or when he or she just wants to be boosted, the user can view all the nice things his or her friends and family have said about him or her on his or her Uplifting Messages page 4000.

Figure 15:
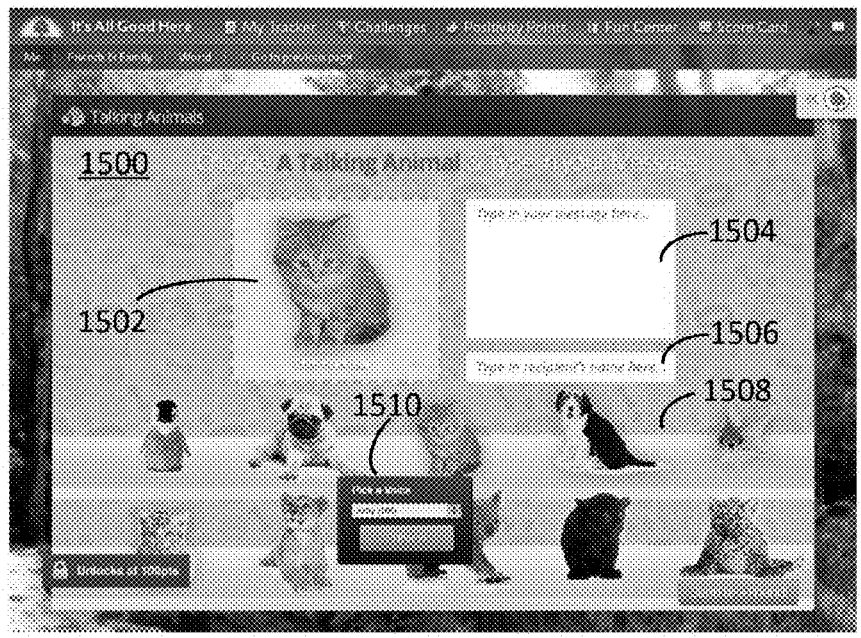
FIG. 15 is an illustrative embodiment of a page for sending a Talking Animals or Clever Critters gift on a social networking website.
Figure 16:
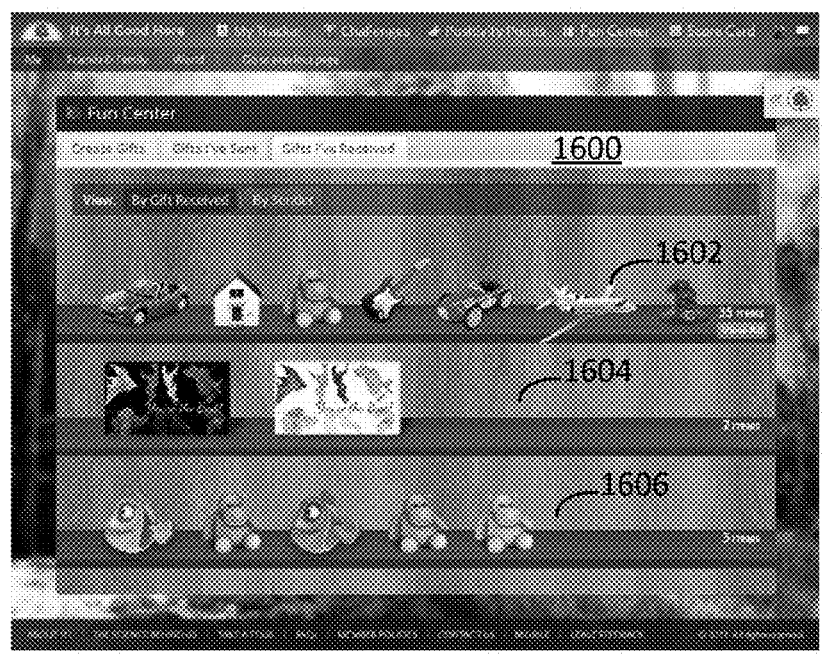
FIGS. 16-18 are illustrative embodiments of a page displaying gifts a user of a social networking website has received.

With respect to FIG. 15, an illustrative embodiment of a page 1500 for sending a gift from the fourth category, Talking Animals (also termed Clever Critters), is shown. The page 1500 comprises a text box 1504 where a user may type a message to send to one of the user's friends. The user enters the friend's name in a second text box 1506. The user selects an image of an animal from the options 1508 provided on the page 1400. The options may include cute animals such as kittens, puppies, and penguins. The user may select a voice for the animal using a voice selection box 1510. The available voices may include chipmunk, British accent, and southern drawl and may speak in a variety of languages. A preview of the gift appears in the preview box 1502. Once a user has filled out the page, the animal may be sent to one of the user's friends where it will speak the message to the friend in the fun accent when it is opened in the friend's inbox. As discussed above, additional options such as additional animals, voices, or languages may become available as a user gains levels.

With respect to FIGS. 16-19, an illustrative embodiment of a page 1600 in the third subsection, Gifts I've Received, is shown. Gifts in the second and third subsections are displayed in separate rows 1602, 1604, 1606 and may be sorted by categories such as Uplift Gifts, Positive Energy Splashes, Uplifting Messages, and Clever Critters. Users may select an option 1608 to sort gifts either by gift (such as car, house, or guitar) or by sender. In the example shown in FIG. 16, the gifts are sorted by gift.

Figure 17:
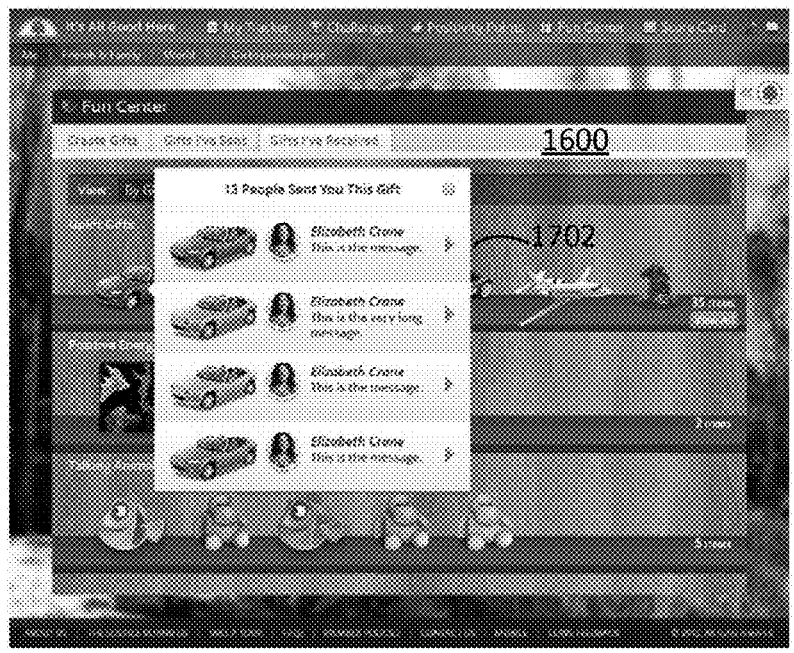

As shown in the illustrative embodiment depicted in FIG. 17, by selecting a particular gift, a box 1702 appears showing the user which of their friends has sent them that particular gift.

Figure 18:
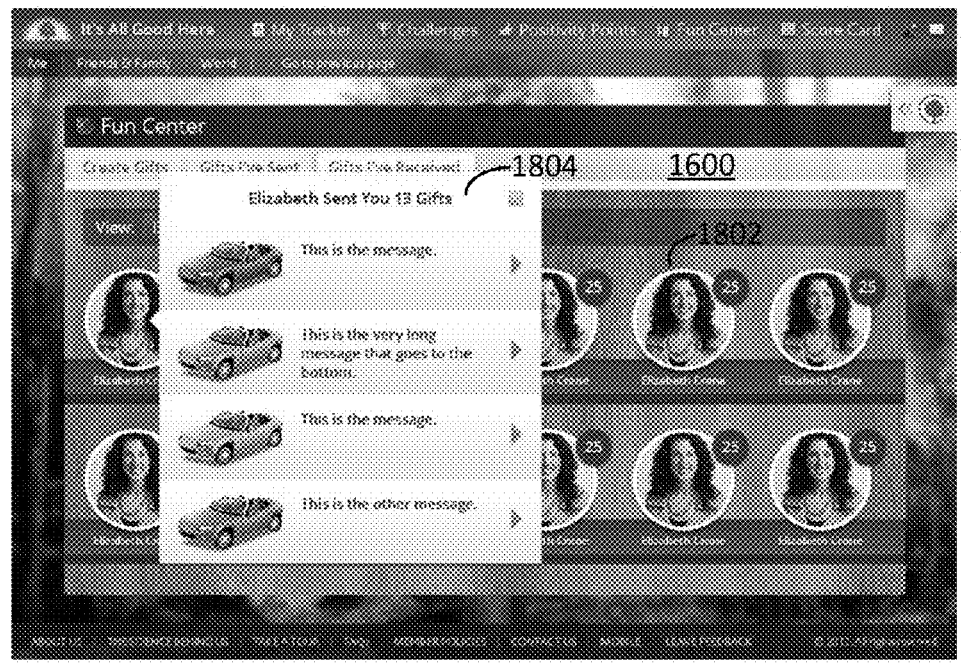

As shown in the illustrative embodiment depicted in FIG. 18, when a user selects the option 1608 to sort gifts by sender, one or more rows of people 1802 are displayed who have sent the user gifts. A user may select one of the people from the one or more rows 1802 to see a box 1804 listing all of the gifts sent by that particular person. In an embodiment, the one or more rows 1802 are sorted alphabetically by the names of the people who have sent the user gifts.

Figure 19:
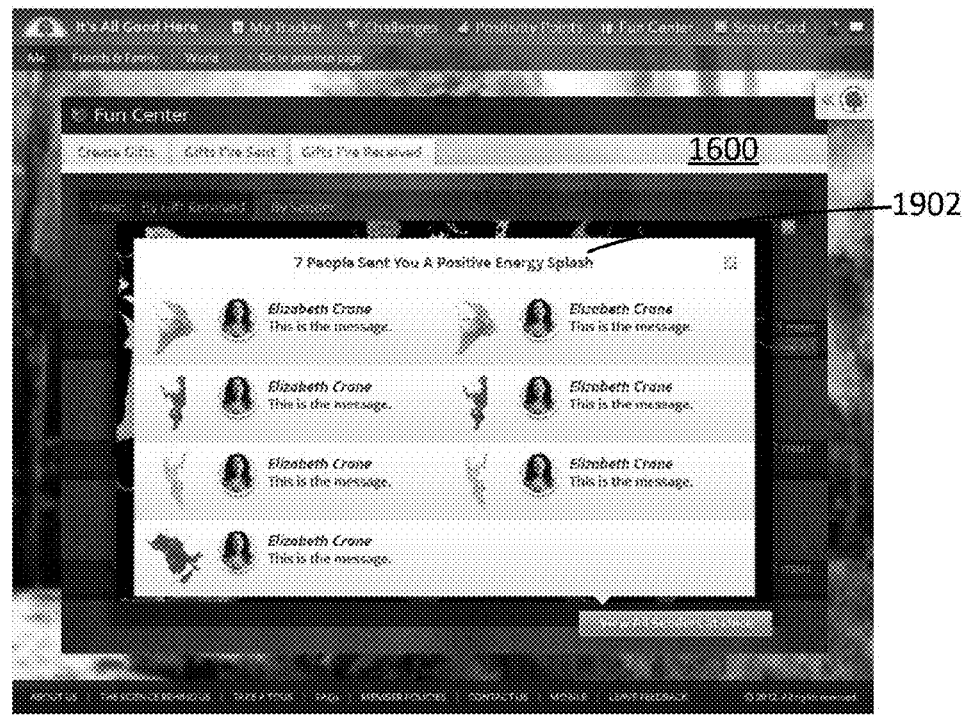
FIG. 19 is an illustrative embodiment of a page displaying all of the users of a social networking website who have contributed to a Positive Energy Splash.

As shown in the illustrative embodiment depicted in FIG. 19, when a user selects a gift that is a Positive Energy Splash, a box 1902 is displayed listing all of the user's friends who contributed to the splash, along with any messages sent by those friends.

The second subsection, Gifts I've Sent, may be organized similarly to the page 1600 displaying the third subsection.

Journals

The website may include one or more journal pages, such as a Gratitude Journal, a Positivity Journal, or a Relief Street journal.

Figure 20:
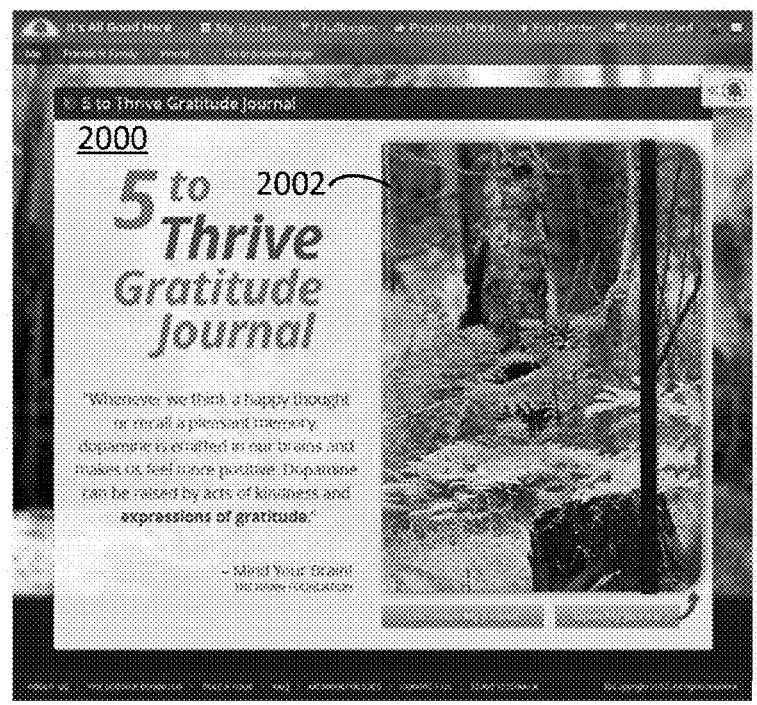
FIGS. 20-22 are illustrative embodiments of a gratitude journal on a social networking website.
Figure 21:
Figure 22:
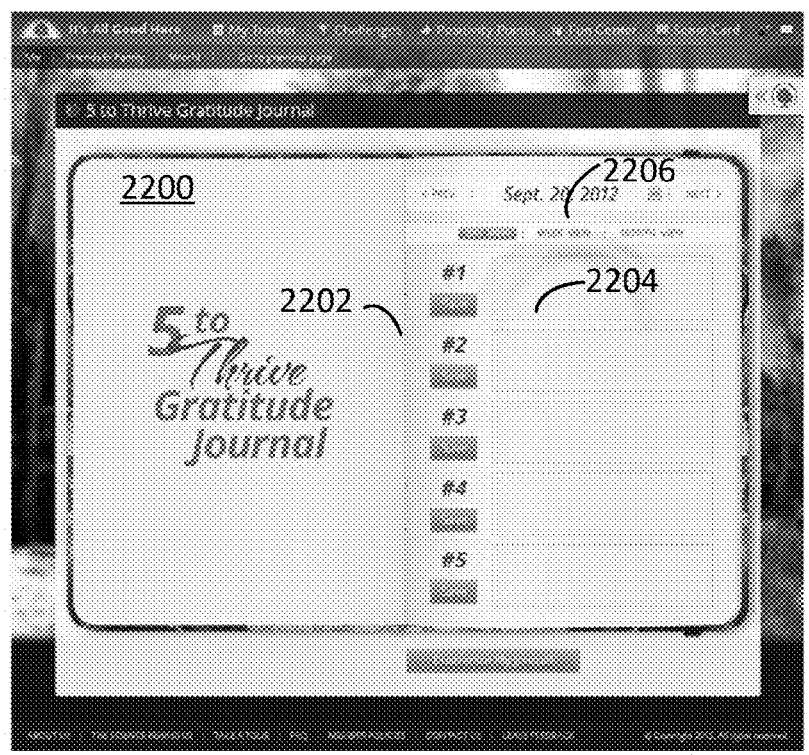

As shown in FIGS. 20-22, an illustrative embodiment of a section of the website containing a gratitude journal, referred to as a "5 to Thrive Gratitude Journal", is shown. As shown in FIG. 20, a main page 2000 of the section contains an image 2002 of a virtual journal. Research shows that if a person writes down five things a day for which he or she is grateful, the person can build a positive brain. Dopamine is emitted in people's brains whenever they think a happy thought or recall a pleasant memory. The release of dopamine causes a person to feel more positive or happy. Accordingly, a brain containing higher levels of dopamine may be referred to as a positive brain, as the person will feel more positive. Dopamine levels can be increased through acts of kindness and expressions of gratitude. Accordingly, a user may use the gratitude journal section to "deposit," or write in the journal, five things for which the user is grateful every day.

As shown in the illustrative embodiment depicted in FIG. 21, a user may use a page 2100 to customize the image 2002 of the Gratitude Journal displayed on the main page 2000, as well as other features of the Gratitude Journal, by using one of the provided pre-made journals 2102. In an alternative embodiment, the user may also upload a custom image to use. Using the options 2104, a user can also customize the journal, including the image 2002 of the Gratitude Journal, for example by adding or removing the strap and the stitching displayed in the main page 2000. Similarly, the user may use the options 2104 to change the font and type of paper in the interior 2202 of the journal (shown in FIG. 22). As the user selects options, a preview 2106 of the journal appears on the page 2100. These options allow a user to personalize their journals, increasing the user's desire to use the journal on a daily basis.

As shown in FIG. 22, the interior 2202 of the journal includes five spaces 2204 for a user to record things for which the user is grateful. The interior 2202 also includes space 2208 for the user to write a journal entry or read previous journal entries. This information displayed in the space 2208 will change based on which content is selected. For example, content may be selected by chapter 2204 or subheading 2206. Similarly, a user can look through past journal entries by clicking on the day, week, or month view options 2206. Additional view options may also be provided, such as, for example, by year, by topic, or by page.

Figure 23:
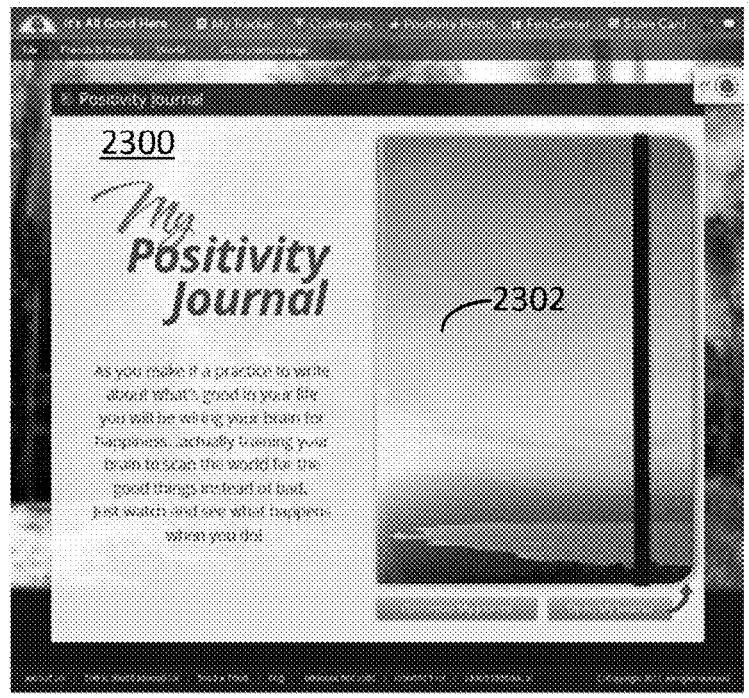
FIGS. 23-25 are illustrative embodiments of a positivity journal on a social networking website.
Figure 24:
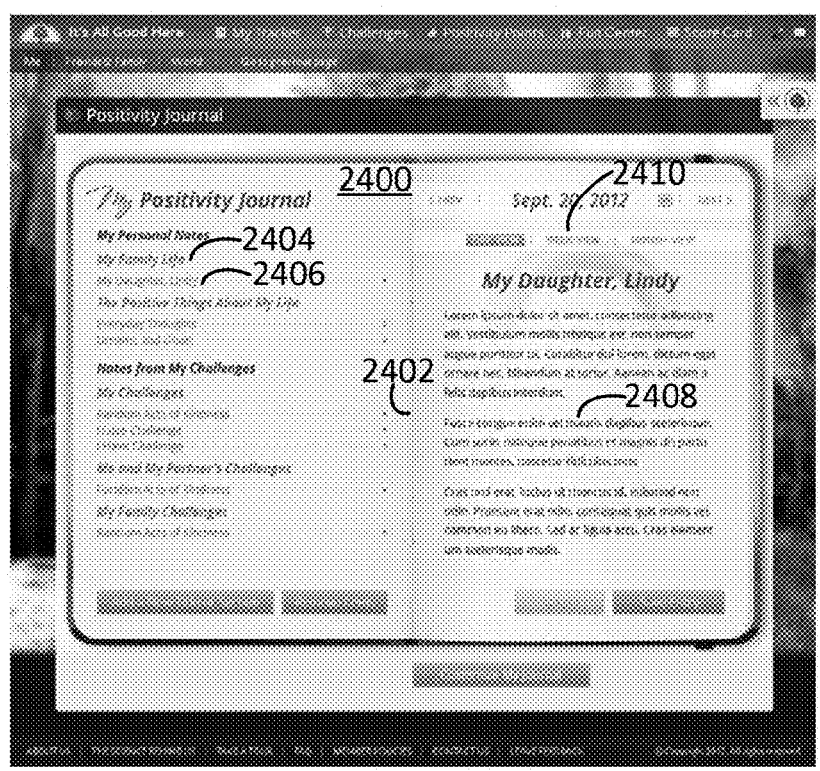
Figure 25:
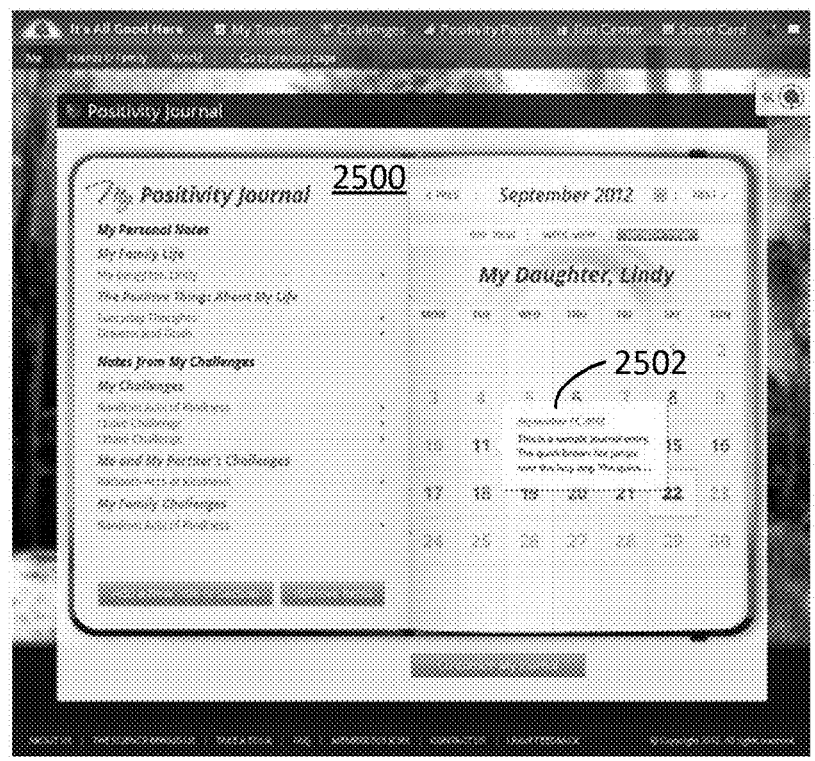

With reference to FIGS. 23-25, an illustrative embodiment of a subsection of the website containing a Positivity Journal is shown. As shown in FIG. 23, a main page 2300 of the section contains an image 2302 of a virtual journal. Research has shown that by spending at least two minutes a day for twenty-one days in a row writing about things that have gone well during the day, a person can begin to rewire his or her brain for happiness. By spending time consciously focusing on positive things every day, a person's brain begins to unconsciously seek out more and more positive experiences. The Positivity Journal subsection provides users with a place to record those things that are positive in the users' lives.

A user may customize a Positivity Journal similarly to a Gratitude Journal, as discussed above. This allows a user to personalize the journal, increasing the user's desire to use the journal on a daily basis.

As shown in the illustrative embodiment depicted in FIG. 24, a page 2400 may display the interior 2402 of the journal, including customizable chapter headings 2404 and subheadings 2406. In an embodiment, when a user takes a challenge (discussed below) that requires the user to write in the user's Positivity Journal, the website will automatically add the necessary chapters headings 2404 and subheadings 2406 for the challenge and create a virtual "page" on which the user may write. Further, the website will automatically track whether the user has accomplished the challenge. The interior 2402 also includes content space 2408 for the user to write a journal entry or read previous journal entries. This information displayed in the content space 2408 will change based on which content is selected. For example, content may be selected by chapter 2404 or subheading 2406. Similarly, a user can look through past journal entries by clicking on the day, week, month or year view options 2410. Additional view options may also be provided, such as, for example, by year, by topic, or by page.

Referring to FIG. 25, an illustrative example of a month view 2500 of the journal is shown. By selecting an individual day, a summary 2502 of the journal entry for that day is displayed.

Favorite Things

In accordance with an embodiment of the present invention, the website may comprise a section titled "My Favorite Things." In this section, a user may view a customized collection of items that make the user happiest. A user may upload and store inspirational media such as their favorite photographs, quotations, videos, articles, and music. The website can automatically generate customized inspirational videos using uploaded media, such as quotes, photographs, and music.

In accordance with an embodiment of the present invention, a user may download and install a standalone application (also termed an "app"), which may be called "It's Good," onto a local device. The application automatically categorizes and uploads media selected by the user, such as photographs, quotations, videos, articles, and music. For example, while a user is browsing the Internet, he or she may encounter an inspirational article. By selecting the article and activating the application, the application will automatically categorize the article and upload it to the user's "My Favorite Things" section of the website. In an embodiment, the application appears as an icon in the user's start bar on the Microsoft Windows operating system.

Mood Flippers

In accordance with an embodiment of the present invention, the website may include a section titled "Mood Flippers." A mood flipper is a tool designed to assist a user in flipping the user's mood, that is, in changing the user's mood from a negative mood to a positive mood. Mood flippers may have different themes, such as, for example, Nature Flips, Relaxation Flips, Man Cave Flips, Inspirational Flips, Get It Off Your Chest Flips, Faith Flips, and Seeing Red Flips. A mood flipper may be placed on a page of the website.

All of the different themes of mood flippers are designed to help a user to feel better and either quickly change from a negative mood to a positive mood or to generally feel good. Users have the option of selecting pre-made mood flippers or customizing mood flippers. In an embodiment, users may select mood flippers created by their friends or by the community of users at large. Accordingly, a user may share his or her custom mood flippers with his or her friends or with the community of users at large.

Figure 26:
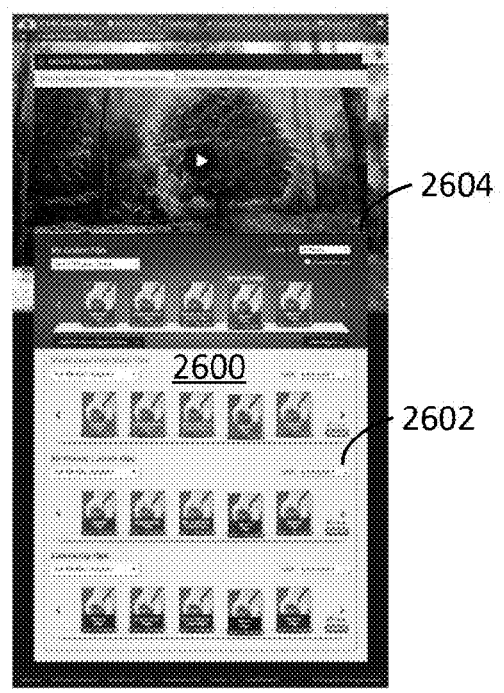
FIG. 26 is an illustrative embodiment of a Mood Flipper page on a social networking website.

As shown in the illustrative embodiment depicted in FIG. 26, the Mood Flipper section may include a main page 2600 displaying available themes 2602 of mood flippers. When a particular theme is selected, an inspirational video or photographs accompanied by music are displayed in a box 2604. This box 2604 may show, for example, a preview of the selected theme. By selecting the box 2604, a user may access a full-sized version of the selected mood flipper and use the mood flipper.

Figure 27:
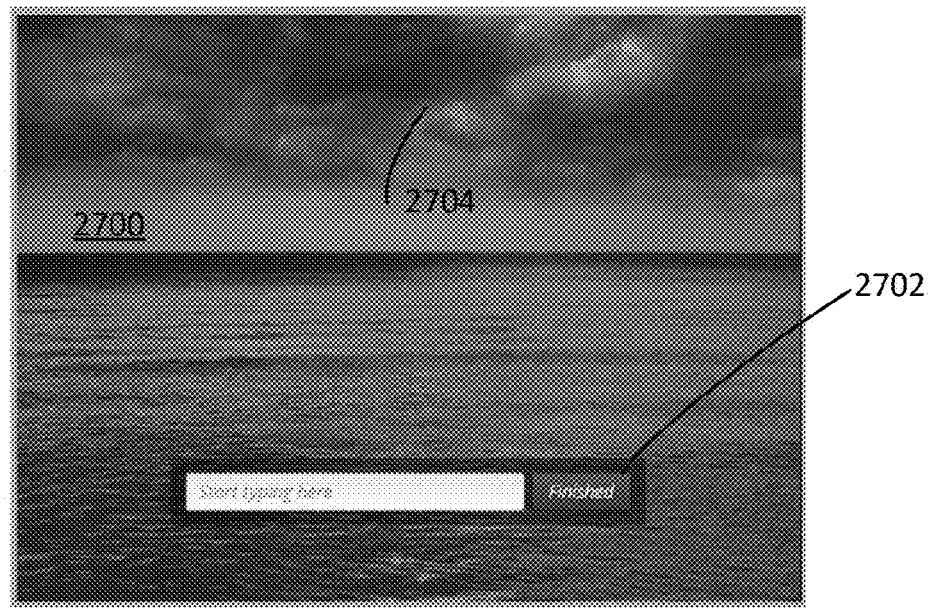
FIGS. 27-28 are illustrative embodiments of a Get It Off Your Chest mood flipper.
Figure 28:
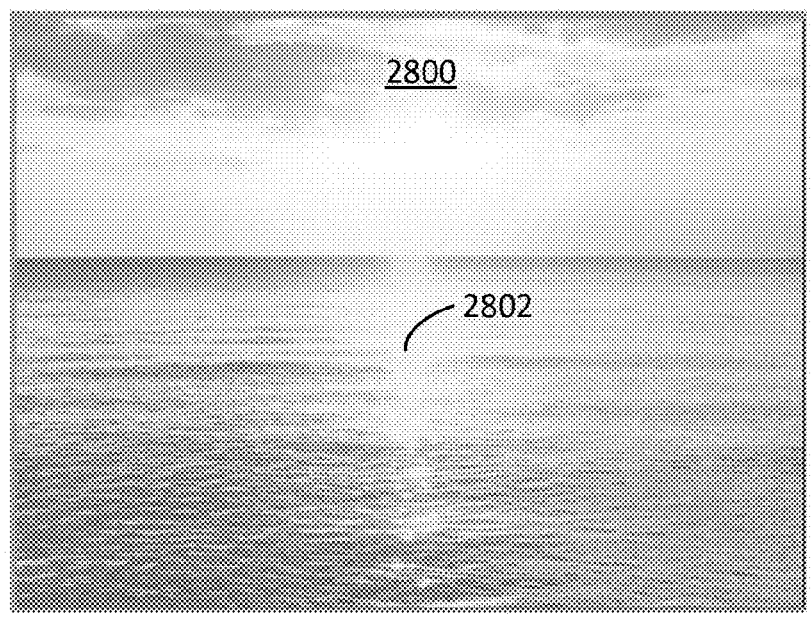

As shown in the illustrative embodiment depicted in FIGS. 27 and 28, one possible type of mode flipper is called Get It Off Your Chest. A Get It Off Your Chest mood flip may take the form of a page 2700. The page 2700 include a text box 2702. With this type of mood flip, a user is able to type his or her worries, upsets, angry feelings, and depressing thoughts into the text box 2702. While the user is typing in the text box, 2702, an animation appears in which, for example, the words fly out of the text box 2702 into an image 2704 above the text box 2702, such as, for example, a storm cloud or a tornado. In an embodiment, the image 2704 grows darker and more ominous as the user types, symbolizing the negativity contained in the words entered into the text box 2702. When the user has finished typing, the page 2700 may show an animation of the image 2704 calming down and transition to a page 2800 containing a peaceful image 2802, such as, for example, the sun shining on calm water. The page 2800 may also play a sound such as, for example, birds chirping. In an embodiment, a message is then displayed congratulating the user. The message may be, for example, "Consider Yourself Heard" or "Good Job Getting That Off Your Chest." This style of mood flipper serves as a dumping ground for a user to get the negative feeling off his or her chest. As the animated scene turns calm in response to the user finishing entering his or her thoughts, the user receives release and is similarly calmed.

Relief Street

In a section of the website referred to as "Relief Street," a user may access a series of videos, each addressing a different difficult experience a person might go through. For example, videos may be on topics such as dealing with the death of a loved one, sexual abuse, illness, heartbreak, bullying, or addiction. After viewing a video, a user may write a response in one of his or her journals on the website. The website may automatically generate a journal page, complete with chapters and subheadings, for each video viewed by a user.

Figure 29:
FIG. 29 is an illustrative embodiment of the main page of a Relief Street section of a social networking website.

As shown in the illustrative embodiment depicted in FIG. 29, the Relief Street section may include a page 2900 with a selection of videos 2902 organized into categories 2904. As will be apparent to one of skill in the art, a different name may be used for the Relief Street section, such as Survival Stories. A preview window 2906 on the page allows a user to preview a video. The categories 2904 may be determined based on topics addressing difficult experiences. By selecting one of the categories 2904, a user may locate videos on a particular topic. The videos, for example, may be testimonials from people who have survived a particular difficult experience. These testimonials offer hope to users by demonstrating that others have undergone similar challenging experiences and flourished afterwards.

In an embodiment, users may upload their own videos regarding experiences they have had. A user can then share their videos with their friends on the website or with the community of users at large. Similarly, users may view videos uploaded by either their friends or by the community at large.

Figure 30:
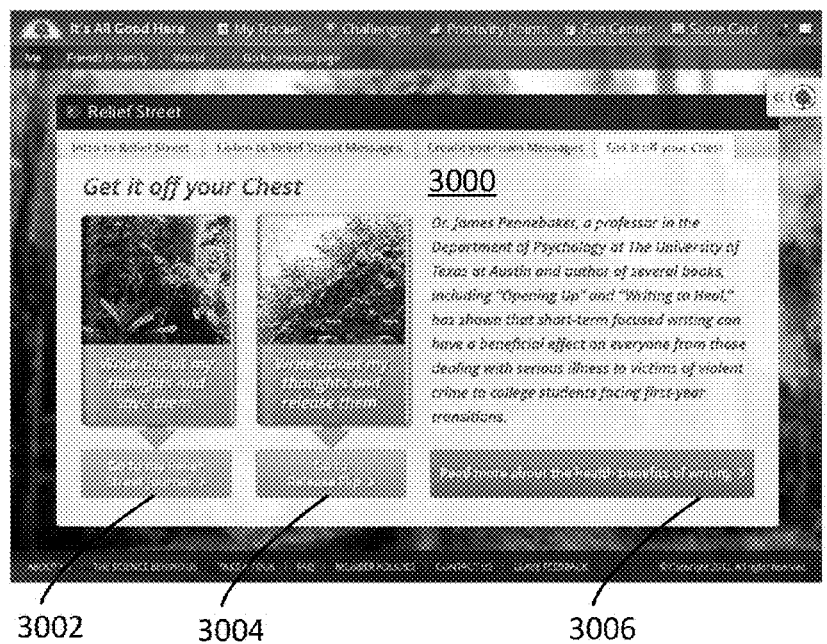
FIG. 30 is an illustrative embodiment of a page containing a mood flipper in the Relief Street section of a social networking website.

As shown in the illustrative embodiment depicted in FIG. 30, within the Relief Street is a page 3000 for assisting a user in releasing pent-up emptions and thoughts. In the example shown in FIG. 30, the page is titled "Get It Off Your Chest." This page may contain, for example, a mood flipper such as the mood flipper termed Get It Off Your Chest. Once a user has viewed a video, they may use this page 3000 to either write about his or her reaction to the video in a journal 3002 or use a Mood Flipper 3004 to improve his or her mood. For example, a user may experience painful emotions upon hearing a testimonial from a survivor regarding a challenging experience the user has endured. By using the page 3000, the user can immediately begin addressing these painful emotions. This enables a user to immediately work to control his or her mood. In an embodiment, the journal 3002 is a Relief Street Journal, which comprises all of a user's reactions to videos on the website. In an embodiment, the page 3000 also comprises an informational section 3006 wherein a user may learn more about the health benefits of writing regarding painful or negative emotions. This section 3006 may include a link to a separate page with additional information.

Challenges

In a section of the website referred to as "Challenges," a plurality of challenges are organized for users to use to challenge themselves to improve their moods. Each challenge is an exercise requiring a user to perform actions over a period of time. By performing the challenge, the user will act to modify their brain in one of a variety of ways. For example, in a twenty-one day challenge, a user may be required to write for two minutes every day about a positive experience he or she has had that day. Research has shown that by spending at least two minutes a day for twenty-one days in a row writing about things that have gone well during the day, a person can begin to rewire his or her brain for happiness. By spending time consciously focusing on positive things every day, a person's brain begins to unconsciously seek out more and more positive experiences. In another example, a user may be required to write down five things a day for which he or she is grateful. Research has demonstrated that by doing this, a user will increase the Dopamine level in his or her brain, thereby causing the user to feel happier and building a positive brain. In other words, by performing particular actions on a regular basis, a person may modify the structure, neurochemistry, and functionality of his or her brain.

In an embodiment, for each challenge a user completes, the user is awarded a number of Positivity Points. Positivity Points may also be awarded for partially completing a challenge.

Figure 31:
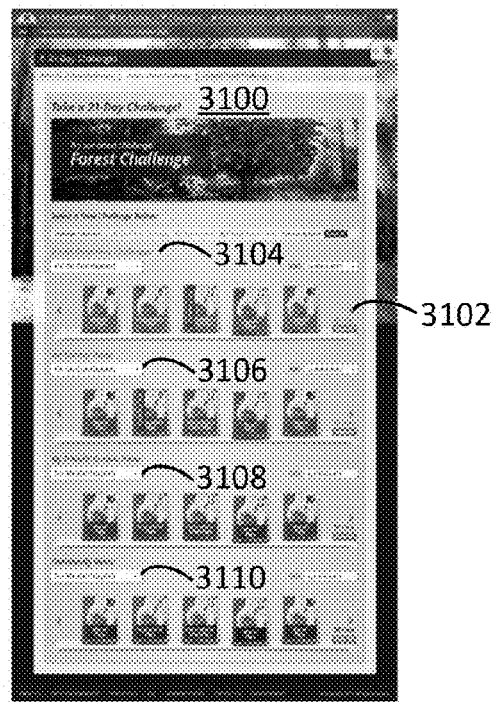
FIG. 31 is an illustrative embodiment of a Challenges page of a social networking website.

As shown in the illustrative embodiment depicted in FIG. 31, on a page 3100 challenges 3102 may be sorted into categories 3104, 3106, 3108, 3110. In an embodiment, challenges may be sorted into categories according to whether they were created by the website 3104, by a particular user 3106, by the user's friends 3108, or by the community of users at large 3110. Challenges 3102 may be created and viewed in video format or in text format, and the challenge page 3100 may also provide users with summaries of how many users have taken each particular challenge, how many are currently taking each particular challenge, and how many of a user's friends are taking each particular challenge. In this way, a user may choose to perform the same challenges as his or her friends or other users. This allows users to mutually support one another by taking the same challenges. Additionally, merely by knowing that other users are taking the same challenge, a user may obtain a motivational boost to complete the challenge. This assists a user in completing a challenge, thereby rewiring his or her brain and making lasting improvements to his or her mood.

Figure 32:
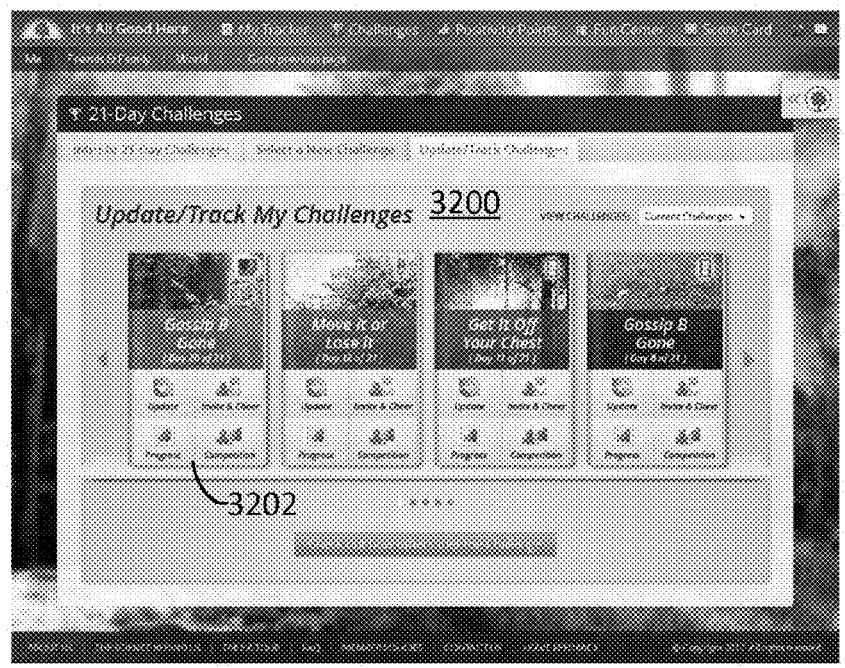
FIG. 32 is an illustrative embodiment of a page that allows a user to track challenges on a social networking website.

As shown in the illustrative embodiment depicted in FIG. 32, in an embodiment, each user is able to update and track his or her challenges 3102 using a My Challenges page 3200. In an embodiment, there are two types of challenges: automatic challenges and manual challenges. Automatic challenges are tracked automatically by the website, as the challenges call for users to perform actions on the website itself, such as, for example, writing in a Gratitude Journal on a daily basis. By monitoring a user's progress on a challenge, the website can automatically award the user with the correct number of Positivity Points, for example based on whether the user completed some, all, or none of the challenge. A user may view his or her progress for each challenge by selecting the Progress button 3202, which causes the website to display the user's progress on that challenge (discussed below).

Figure 33:
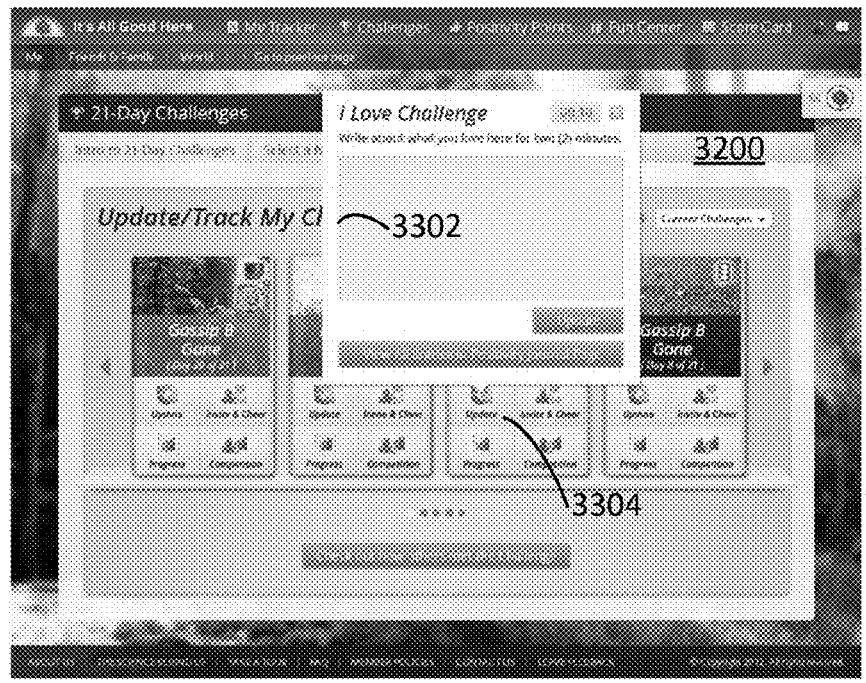
FIG. 33 is an illustrative embodiment of the process for updating an automatic challenge on a social networking website.

As shown in the illustrative embodiment depicted in FIG. 33, for an automatic challenge, the My Challenges page 3200 displays a box 3302 when a user clicks an update button 3304. This box 3302 enables a user to write whatever the user is required to write for a given challenge directly on the page 3200. The website may automatically store the user's writing in the appropriate one of the user's journals, such as the user's Positivity Journal. For example, a challenge may be to focus during the day on the things that a user loves and then write about the things the user loves for at least two minutes during the day. When the user is ready to write, the user merely clicks the update button 3304 and writes in the box 3302. The website will automatically credit the user for performing the challenge and will track the user's progress in completing the challenge.

In contrast, a manual challenge is a challenge that a user performs apart from the website. In an embodiment, a user may access the website every day during the challenge and manually report whether the user finished some, all or none of the challenge. The user can view his or her progress over the course of the challenge on a calendar and also on a graph. Positivity Points are awarded based on how a user performs on the challenge. For example, completing an entire challenge may be worth ten points, completing some of a challenge only five points and completing none of a challenge zero points. The number of points awarded per challenge and per day may be tracked on a graph. In an embodiment, a user may also upload a testimonial explaining how a particular challenge has impacted his or her life. These testimonials may be displayed on the challenge page 3200 next to the respective challenge 3102. This assists each member of the community of users at large in determining which challenges 3102 are the most relevant to him or her.

Figure 34:
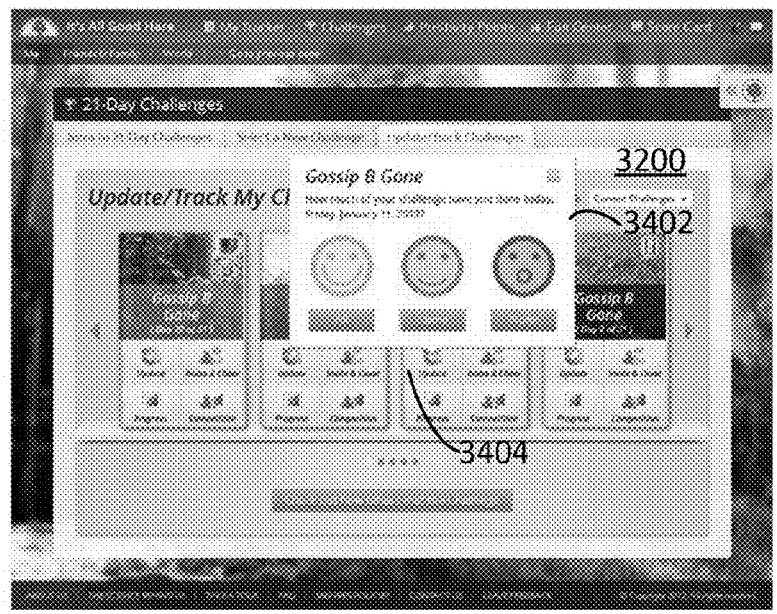
FIG. 34 is an illustrative embodiment of the process for updating a manual challenge on a social networking website.

As shown in the illustrative embodiment depicted in FIG. 34, when a user selects the update button 3404 on the challenge page 3200 for a manual challenge, a box 3402 appears wherein a user may report his or her progress on the challenge. For example, at the end of each day, when a user taking a manual challenge accesses the challenge page 3500 and selects the update button 3404, the box 3402 will ask if the user completed some, all, or none of the challenge. When the user selects the appropriate option in the box 3402, the website will record the user's score and track the user's progress.

Figure 35:
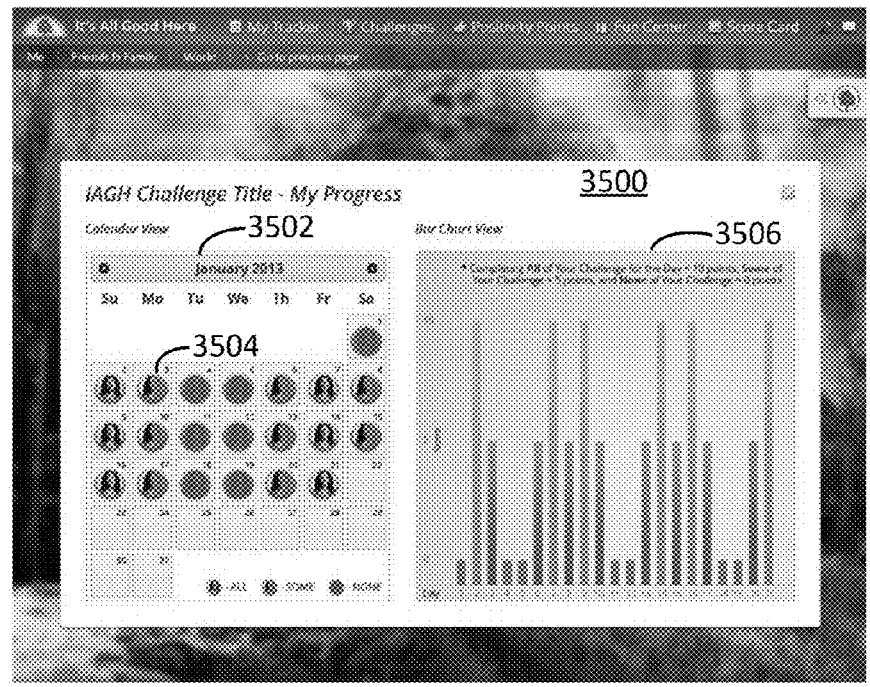
FIG. 35 is an illustrative embodiment of a page displaying a user's progress on a particular challenge on a social networking website.

As shown in the illustrative embodiment depicted in FIG. 35, a user may visit a Challenge Progress page 3500 to view his or her progress on a particular challenge. The Challenge Progress page 3500 may include a calendar 3502 showing an icon 3504 for each day of the challenge. The icon 3504 represents the user's progress on the challenge, such as, for example, whether the user completed all, some, or none of the challenge on that day. A bar chart 3506 may indicate the number of points a user was awarded on each day. For example, as shown in FIG. 35, by completing none of the challenge on day 1, the user was awarded zero points. By completing all of the challenge on day 2, the user was awarded ten points. By completing some of the challenge on day four, the user was awarded five points. Other graphs may also be used to indicate the number of points received by the user on each day of the challenge.

Figure 36:
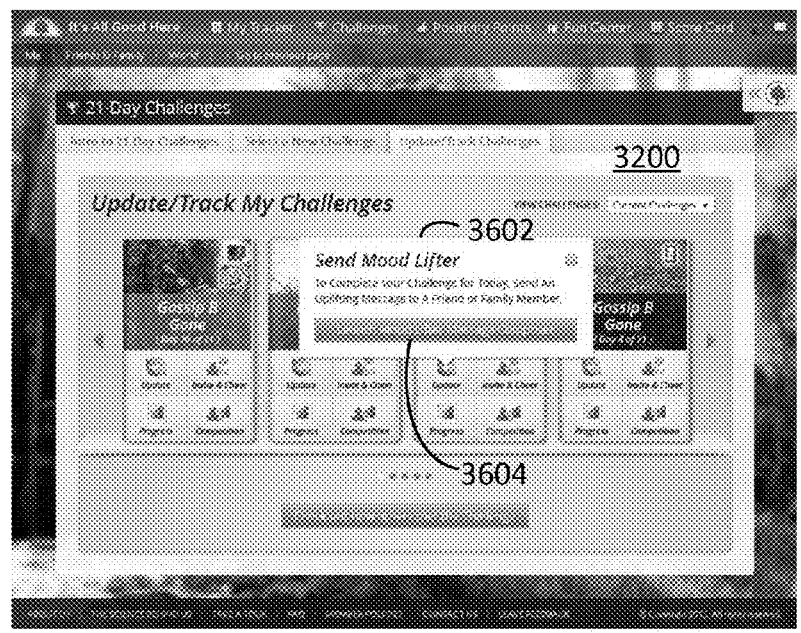
FIG. 36 is an illustrative embodiment of a page containing an alert instructing a user to complete a challenge on a social networking website.

As shown in the illustrative embodiment depicted in FIG. 36, if a user has not completed a challenge for a particular day and accesses the challenge page 3200, a box 3602 will appear, instructing the user to complete their challenge for the day. In an embodiment, the box 3602 contains instructions on how to complete the challenge for the day. In an embodiment, the box 3602 also contains an update button 3604 that takes the user directly to a page where the user may complete the challenge, for example, to one of the user's journals.

In an embodiment, challenges may be twenty-one days in length. In another embodiment, challenges may last for thirty, sixty, or ninety days in order to build a user's feelings of self-worth and good mental health. These longer challenges may help improve a user's inner and outer well-being. For example, longer challenges may include drinking eight glasses of water a day, getting thirty minutes of exercise a day, or writing every day about positive experiences the user has had.

Fabulous Future

Figure 37:
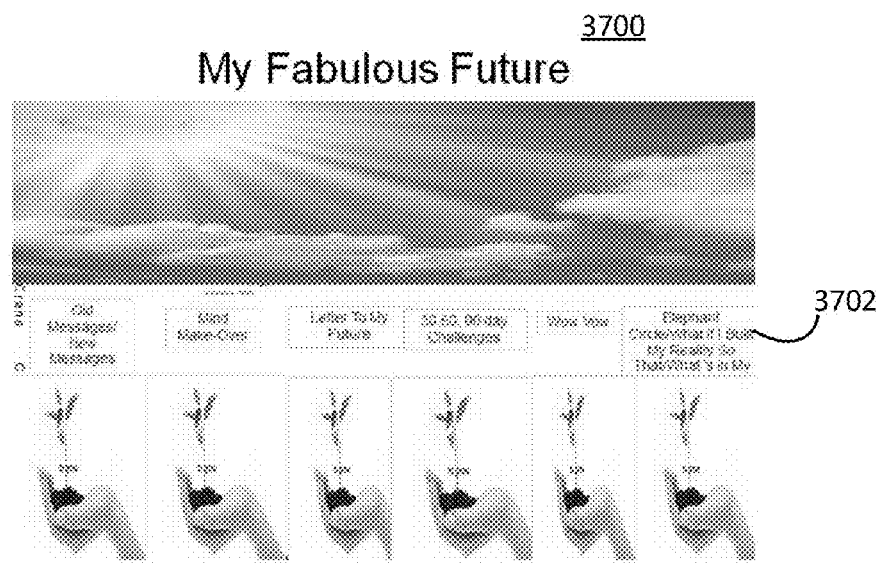
FIG. 37 is an illustrative embodiment of a main page of a Fabulous Future section of a social networking website.

As shown in the illustrative embodiment depicted in FIG. 37, my Fabulous Future is a section of the website that helps users accomplish their goals for the future and improve their outlook on life. In an embodiment, a main page 3700 of the section lists various kinds of self-improvement exercises 3702. Each exercise 3702 is designed to help boost a user's self-esteem and build his or her resilience. As discussed above, exercises are capable of rewiring a person's brain. Accordingly, an exercise 3702 accomplishes these goals by building neural nets in a user's brain between the user's left prefrontal cortex to and the user's amygdala, thereby making the user more resilient and happy. An exercise 3702 will also give a user tools to help the user have their best possible life. For example, an exercise 3702 might help a user to develop strategies for coping with negative feelings, such as by using a mood flipper.

In an embodiment, one exercise 3702 entitled "Old Messages/New Messages" requires a user to write down all of the negative messages that the user says to him or herself and then write a new list reflecting the user's preferred reality. Every day, when the user accesses the exercise 3702, a message from the new list is displayed. By repeating one or more of these messages every day, the user will program his or her subconscious mind. By repeating these messages, the reticular activation system in the brain in charge of filtering information starts to scan the environment for proof of the new messages. The brain understands the new messages are important because of how often the messages are repeatedly being programmed into the mind. It is a powerful practice that is made simple for people to use through the website.

In an embodiment, an exercise 3702 referred to as "Letter to My Future" has a user write a letter to himself or herself about the user's hopes and dreams along with commitments or steps the user will take to reach the user's hopes and dreams. A user will then be presented with this letter at whatever interval the user selects in order to remind the user of his or her commitments and progress. This assists a user in being accountable to himself or herself. Similarly, the repetition trains the user's brain to focus on the importance of the user's goals and hopes.

In an embodiment, an exercise 3702 referred to as "Wow Vow" guides users through making a vow to themselves to be good to themselves through sickness and in health, much like a traditional marriage vow. This exercise may teach users that in tough times, they deserve the same commitments, for example to treat themselves well and love themselves forever, that they would give to another person. In other words, users learn that they must love themselves and support themselves, rather than blaming themselves or bullying themselves for perceived flaws.

In an embodiment, an exercise 3702 referred to as "Elephant Circle" guides users in examining their limiting beliefs and helps them push past their boundaries to live up to their fullest potential.

In an embodiment, an exercise 3702 referred to as "What If I Built My Reality So That . . . " helps users look deeper into their limiting beliefs and to try on some healthier ones that can help them make great shifts into living their best life.

In an embodiment, an exercise 3702 referred to as "What's in My Cake?" helps users to evaluate their inner selves by walking through the process of imagining themselves as a cake. By doing this, users assess whether the frosting on their cake (the part of themselves that is easily visible) is covering up a cake whose inner ingredients are not so good or if they are covering up an incredibly delicious treat. In other words, users evaluate the health of their inner selves and whether their inner selves are full of positivity or negativity. By evaluating whether deep inside they have negative feelings, such as, for example, feeling insecure, discouraged, or jealous, users can utilize the tools offered on the website to address their particular negative feelings.

With My Friends and Family

In an embodiment, the website includes a section referred to as "With My Friends and Family." This section may be reached using the segment 304 on the main page 300. This section is designed to assist users in helping improve the moods of their friends and family.

Figure 38:
FIG. 38 is an illustrative embodiment of a main page of a With My Friends and Family section of a social networking website.

As shown in the illustrative embodiment depicted in FIG. 38, the With My Friends and Family section includes a My Friends and Family page 3800 containing a plurality of themes for uplifting messages 3802. The My Friends and Family page 3800 may, for example, contain an image of a tree with uplifting message themes 3802 in its leaves. Each uplifting message theme 3802 may be a theme such as, for example, "If I Haven't Told You Lately . . . " or "You're Awesome!". This page allows a user to send a message to another user on the website.

Figure 39:
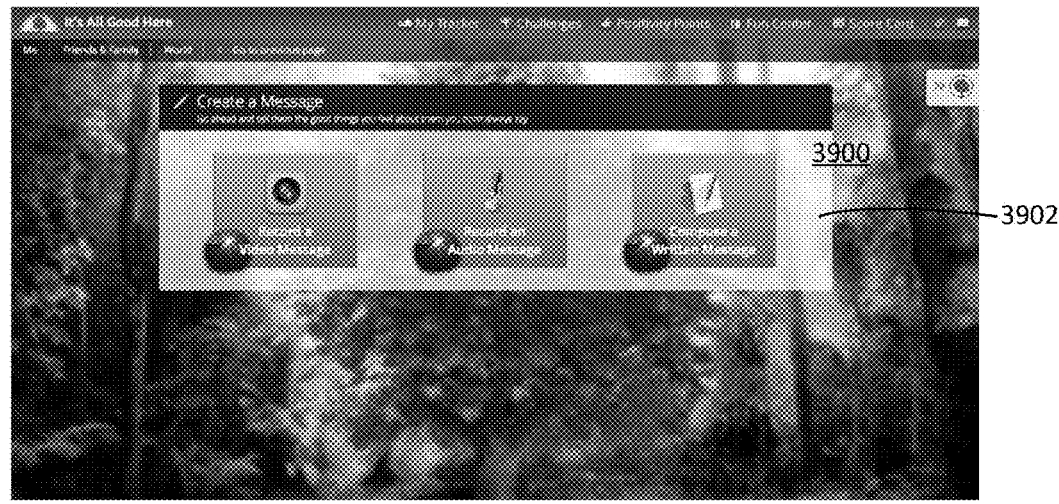
FIG. 39 is an illustrative embodiment of sending an uplifting message on a social networking website.

As shown in the illustrative embodiment depicted in FIG. 39, when a user selects an uplifting message 3902, the user is presented with a page 3900 containing a box 3902 allowing the user to select the type of message to send. For example, a user may choose to leave a video, audio or text message based on the particular theme of the selected message. For example, by selecting a message theme of "You're Awesome!", a user can choose to send a video, audio, or text message to another using telling the other user how awesome he or she is. In an embodiment, the uplifting message 3902 is termed a "Meaningful Message." In another embodiment, the uplifting message 3902 is termed a "Mood Lifter."

Once sent, the message will show up in the other user's inbox on the website and can be saved to the other user's Uplifting Messages page 1400. The other user can then visit the Uplifting Messages page 1400 whenever he or she feels he or she needs a boost.

Figure 40:
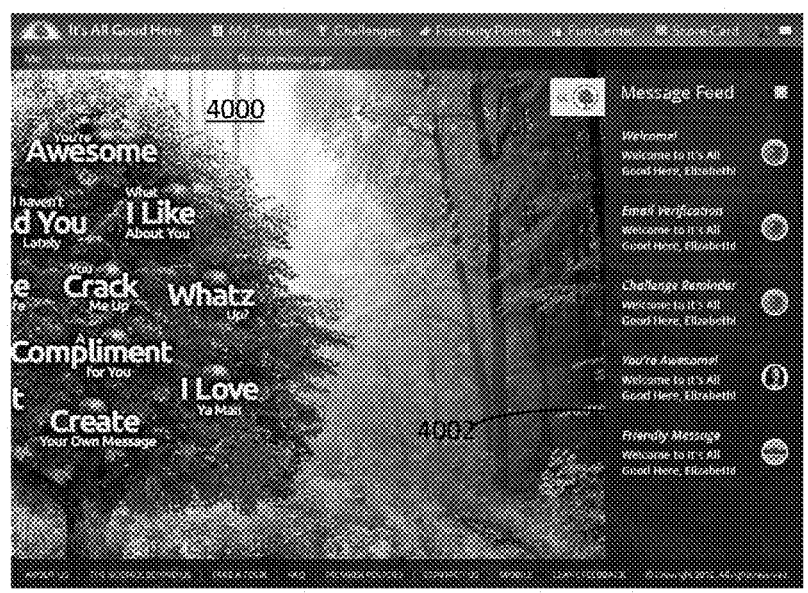
FIG. 40 is an illustrative embodiment of a combined inbox/message feed on a social networking website.

As shown in the illustrative embodiment depicted in FIG. 40, the My Friends and Family page 4000 may also contain a combined inbox/message feed 4002. The feed 4002 displays gifts and messages a user has received from his or her friends. A user can then reply to a message or gift in the feed 4002 by sending a message or gift in return. The feed 4002 may also contain announcements or alerts regarding to the website, the user, and the user's friends. For example, the feed 4002 may contain alerts indicating a friend has posted a mood flipper or taken a new challenge, or indicate that the user has not yet completed a challenge for that particular day. The feed 4002 may aggregate responses posted by multiple users to a particular alert. For example, if a first user begins a new challenge, the feed may contain replies from several of that user's friends offering encouragement with the challenge. These replies are visible in the feeds 4002 of each of the first user's friends.

My Profile

In an embodiment, each user of the website may create an individual profile page displaying information about the particular user.

Figure 41:
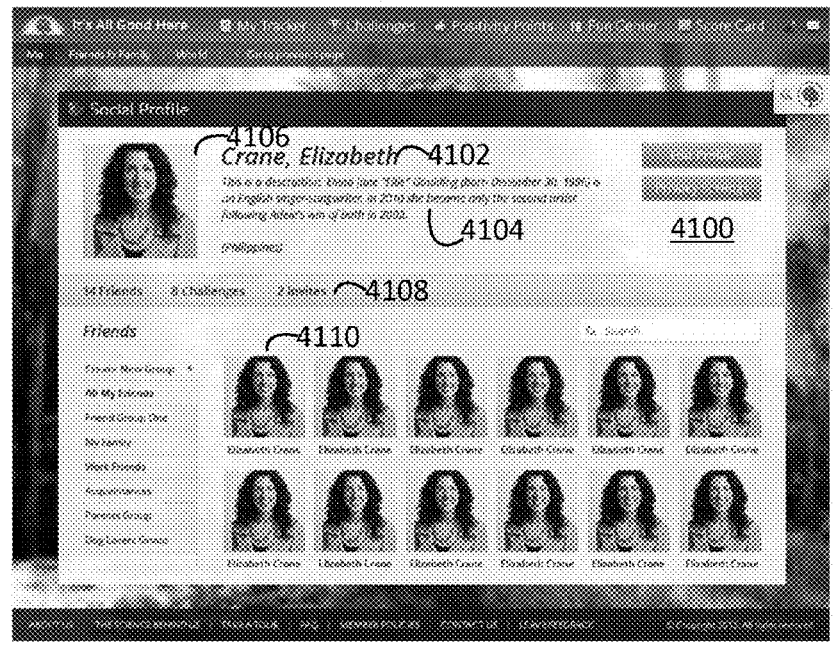
FIG. 41 is an illustrative embodiment of a social profile page on a social networking website.

As shown in the illustrative embodiment depicted in FIG. 41, a Profile page 4100 may contain a user's name 4102, brief biography 4104, and a photograph 4106. The Profile page 4800 may comprise an alert bar 4108 listing alerts such as, for example, the number of other users who have added the user as a friend, the number of challenges the user is taking, and the number of other users who wish to add the user as a friend. The page may further comprise a section 4110 listing all of a user's friends, along with various categories such as, for example, Family, Coworkers, and Acquaintances.

As a social network, IAGH allows a user to invite friends to join IAGH, send other users uplifting messages (including video, audio, and text with emoticons), and post content (such as challenges, mood flippers and Relief Street messages) for their friends and the IAGH community to view. Users may respond to received uplifting messages and various postings on IAGH by either posting in combined inbox/message feeds 4002 or in separate message inboxes. Messages may be either personal (shared between only two users, allowing them to communicate back and forth privately) or public (appearing on message feeds that have groups of users, all able to respond to each other). In an embodiment, a user may provide IAGH with their credential for another social networking website, such as Facebook®, LinkedIn®, and Google+™, in order to have IAGH invite their friends on the other social networking website to join IAGH. IAGH may automatically index a user's friends from another social networking website, in order to automatically create corresponding groups for the user on IAGH. In this way, a user may readily find, post and send messages to their various groups of contacts from other websites.

In an embodiment, a user may also edit their profile, for example, by providing custom information and a custom design.

With Our World

In an embodiment, the website includes a section referred to as "With Our World" or "Uplift Our World." This section may be reached using the segment 306 on the main page 300. This section is designed to assist users in helping improve the moods of the world at large. By doing this, users will simultaneously uplift themselves.

Figure 42:
FIG. 42 is an illustrative embodiment of a main page of a With Our World section of a social networking website.

As shown in the illustrative embodiment depicted in FIG. 42, the With Our World section may include a main page 4200 with sections for good news 4202, global challenges 4204, and Uplift Our World 4204. The good news section 4202 may comprise a curated news station that posts only good news, or news about positive events. In an embodiment, the news section 4202 is administered or monitored by the website automatically. In an alternative embodiment, the news section 4202 is curated by humans. In an embodiment, users may volunteer to assist in curating the news section 4202.

Global challenges 4204 are challenges (that last, for example, twenty-one, thirty, sixty, or ninety days) that are designed to help users have more compassion toward one another, more tolerance, and more knowledge about different cultures. This section serves to emphasize the fact that no matter what differences exist between individuals or groups of people, everyone is similar in the most fundamental and important ways. In an embodiment, global challenges are sorted into categories such as challenges created by the IAGH website and challenges created by a user's friends, and challenges created by the community of users at large.

The Uplift Our World page 4204 is a portal for users to upload and share their ideas on how to uplift the world. This section also features ways for users to concretely improve the world at large. For example, in an embodiment, IAGH users may donate monies to particular charities. These charities may be automatically selected by the IAGH website from a pool of applicant charities based on factors such as, for example, the charities that are found to be the most in line with the goal of uplifting the world. Alternatively, members of the IAGH community may pitch (for example, via a feature on IAGH that permits members to record and upload five minute video messages) their ideas for a for-profit or not-for-profit company whose mission will help to uplift the people and/or the world. If selected and posted, users from the IAGH community can donate monies to the ideas that have been posted that they want to support. All monies will go to IAGH, which will pay a team of people to work with the creator of the idea to build a company whose mission will help to uplift people and/or uplift the world. Once the company is ready to launch, all remaining monies will go to the company and be privately owned by the creator with a contract signed that going forward, a portion of the company's profits (for example, five percent to ten percent) will be funneled back into IAGH specifically to help fund other ideas for further companies that will uplift people and/or the world that are pitched on the IAGH site. In an embodiment, charities may be selected for inclusion by individuals, for example, users who have volunteered or employees hired to assist in running the website. In an embodiment, this section of the website will activate when one million users has joined the website. In an embodiment, this section highlights one or more companies on a regular basis (such as daily, weekly or monthly). Users may then donate money directly to the one or more highlighted companies. In an embodiment, a user may donate money using any known payment method, such as credit card, PayPal™, Amazon Payments™, Western Union®, or another payment system.

Inner Well-Being Games

In an embodiment, IAGH includes one or more games that are designed to build self-esteem and self-worth in individuals playing the games. The games may be played either by single users or by numbers of users simultaneously, such as in a massively multiplayer online game (MMOG), thereby allowing users to play among groups of their friends. In an embodiment, a game includes a segment that requires a user to leave a compliment for another user when he or she reaches a certain part in the game in order to advance in the game.

Alternatively, a user must receive a certain number of compliments from other users in order to advance. In this case, the website may automatically notify a user's friends that they require compliments or positive statements in order to advance. Progressing in or completing a game may award a user one or more Positivity Points.

In an embodiment, the website includes one or more games referred to as "Lifetime Inner Well-Being Games" that are based on the theory that a person becomes an expert at a particular activity when he or she has spent at least ten thousand hours performing the activity. Accordingly, in a Lifetime Inner Well-Being Game, users are rewarded for spending particular amounts of time performing certain activities in order to promote the user spending sufficient time at the activity in order to become an expert. For example, a game may require a user to spend a certain amount of time reflecting upon positive experiences. To do this, the game may incorporate tasks that require the user to, for example, list positive experiences they have had recently.

In an embodiment, the website is configured to interact with a portable device such as, for example, a bracelet or cell phone. In an embodiment, the bracelet is referred to as an "IAGH Positivity Bracelet." Each bracelet includes an identifier that may be scanned every time a user does something they feel positive about. For example, the bracelet may include a microchip including a radio-frequency identification (RFID) chip that may be scanned by a specialized device. Alternatively, the bracelet may include a microchip that may be scanned by another portable device, such as a user's cell phone. By scanning the microchip, the device reports to the website that a particular user has performed a positive action. The user may then be awarded one or more Positivity Points. In an embodiment, the mobile device, such as a cellular phone, includes an application a user may use to report to the website he or she has performed a positive action.

In an embodiment, articles such as clothing or bracelets contain microchips programmed to communicate with one or more devices. By causing a device to interact with one of these microchips, for example, by placing the device in proximity to the microchip, the microchip causes the device to display a secret message to the user. This message may be, for example, a positive message designed to uplift the user. The device may be, for example, a cellular phone or other portable device. The portable device may report to the website that a microchip has been scanned, enabling the website to award one or more Positivity Points to the user.

In an embodiment, the website is configured to display positive messages to a user at either predetermined or random times. These messages are designed to inspire, educate and remind users about elements of the site. For example, a user may receive a message reminding him or her of the benefits of recording things he or she is grateful for in the user's journal on a daily basis. The message may include information such as recent research indicating the benefits of recording such information on a daily basis.

Commercial Platform

In accordance with an embodiment of the invention, a commercial platform or a website exists that is used internally by a particular company in order to improve employee morale, engagement, camaraderie, resilience, and productivity. This commercial platform may be used only by individuals authorized to access the platform. In an embodiment, access may be restricted to employees, for example, by restricting membership to individuals with an e-mail address at a particular domain. In an embodiment, the commercial platform includes a business console that allows a human resources (HR) team at an organization to upload all of the organization's employee information onto the platform. The HR team may control what access employees receive and what functionality is enabled on the corporate platform.

Figure 43:
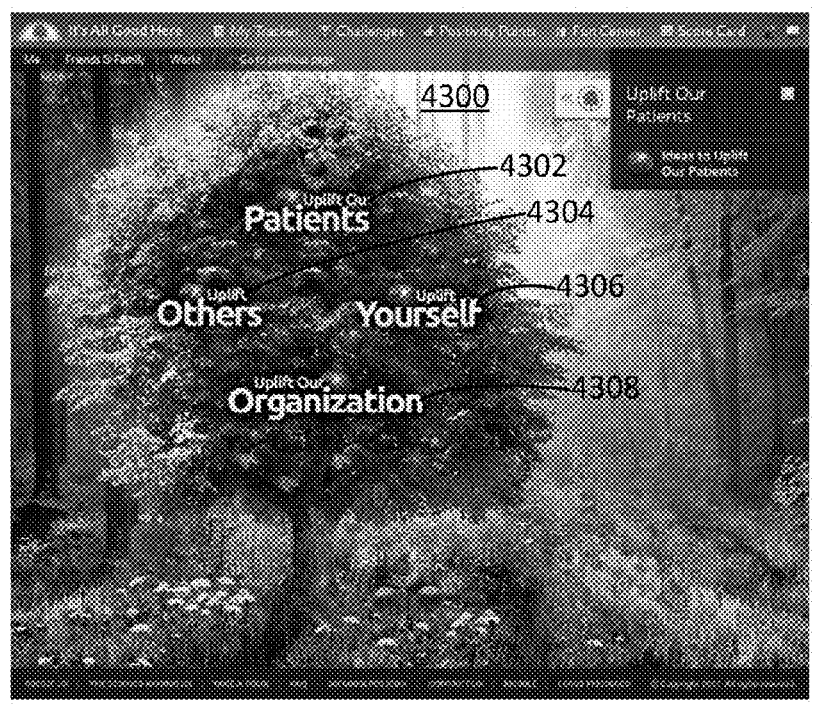
FIG. 43 is an illustrative embodiment of a main page of a commercial platform of a social networking website.

As shown in the illustrative embodiment depicted in FIG. 43, the commercial platform may include a main page 4300 comprising four separate sections: Uplift Our Patients 4302; Uplift Others 4304; Uplift Yourself 4306; and Uplift Our Organization 4308. Uplift Our Patients 4302 may be customized based on the nature of the business by replacing "Patients" with another term such as, for example, "Customers" or "Guests." Uplift Others 4304 may also be termed "Uplift My Coworkers" or a similar name. Uplift Yourself 4306 may also be termed "Uplift My Self" or a similar name. Each section 4302, 4304, 4306, 4308 contains functionalities to uplift the stated audiences similarly to the sections of the public website described above. For example, the Uplift Others section 4304 may allow users to send uplifting messages to coworkers. The section 4304 may also include useful information on how to interact with coworkers in a positive manner. Similarly, the Uplift Our Patients section 4302 may allow a user to send an uplifting message to a patient and could contain information regarding how to positively interact with patients. The Uplift Yourself section 4306 may contain all of the features of the public website. In an embodiment, the Uplift Yourself section 4306 contains a link to the public website.

The commercial platform contains additional customizations, making it more effective in the workplace. For example, in an embodiment the Mood Flippers section main page 2700 may include a mood flipper designed to combat gossip in the workplace, referred to as "Gossip Be Gone." This tool is designed to allow a user to write his or her worries, their upsets, their angry feelings, their depressing thoughts into a text box and then watch the words disappear in an animation. It is designed so that users who want to gossip can dump the gossip into the Gossip Be Gone mood flipper (where it will harmlessly disappear) rather than spreading it in their work environment. This allows a user to vent his or her thoughts or bad feelings without spreading poisonous gossip in their environment. In an embodiment, the Gossip Be Gone mood flipper comprises a picture of a beautiful scene with a text box into which a user may type gossip. As the user types, an animation appears comprising unpleasant colors that slowly cover the screen. These colors reflect the negativity of gossip and the potential for damage to be caused to others by gossiping. This serves to reinforce to the user's brain that gossip is harmful. When a user is finished typing, the unpleasant colors slowly fade from the screen, revealing the picture of the beautiful scene. In an embodiment, a positive message appears such as, for example, "thank you for dumping that here and not spreading that to other people, you are amazing!"; "that was hard, good job!"; or "you did a great job to leave that here!".

In an embodiment, the commercial platform is configured to interact with either a microchip or scannable indicia located, for example, on an employee's name tag. For example, a quick response (QR) code may be located on the back of an employee's name tag. When an employee scans the code, for example by using a portable device such as a cellular phone, the device accesses the commercial platform and performs an action. These actions may include, for example, displaying an uplifting message to the employee, displaying an employee's profile page, and instantly sending an uplifting message to an employee from the employee who scanned the code.

Mood Disorders

Mood disorders, such as, for example, clinical depression and bipolar disorder, may be characterized by prolonged negative moods. Mood disorders may be defined by the Diagnostic and Statistical Manual of Mental Disorders, 4th Edition, Text Revision (DSM-IV-TR; APA, 2000). Mood disorders may result from the particular neurological structure of the brain or the chemistry of the neurotransmitters present in the brain. Further, the neurological structure of a person's brain may determine the brain's neuro-responses to various stimuli. For example, a particular neurological structure or neurochemical balance may prevent a person from feeling happy or joyful. By altering the neurological structure or neurochemistry of the brain, a person may change his or her mood. As such, a physician may treat a person suffering from a mood disorder or from negative moods in general by altering the person's neurological structures or person's neurochemistry. Further, a person suffering from negative moods may similarly alter his or her neurological structures or modify his or her neurochemistry by improving his or her mood.

Therapy and/or medication has long been used to treat mood disorders. However, both may be expensive and burdensome on an individual, requiring him or her take significant steps in order to obtain treatment. By leveraging techniques similar to those used in therapy, a system in accordance with the present invention may be used by a physician as part of a treatment program to help a patient to get relief from the symptoms associated with his or her mood disorder without the significant costs or other burdens generally associated with therapeutic treatment. Similarly, a system in accordance with the present invention may be used to avoid the troublesome or dangerous side-effects often associated with medication.

A person's mood may be quantified as positive or negative based on the subjective feelings of the person. A person's mood may be directly related to the person's neurological structure or the chemistry of neurotransmitters present in the person's brain. As a self-reporting quiz may be cheaper, quicker, and less invasive than measuring the structure or chemistry of the brain, such self-reporting quizzes may preferably be used in some cases to quantify a person's mood. For example, a physician may use a self-reporting quiz to track a person's mood, and thus indirectly monitor changes in his or her neurological structure or neurochemistry, as a supplement to other diagnostic methods such as CT scans or MRIs. Further, improving a person's mood, positivity, and resilience levels may positively impact the neurological structure and neurochemistry of the person's brain.

In an embodiment, a system in accordance with the present invention is used to treat mood disorders such as, for example, by altering the neurological structure or neurochemistry of the brain so as to treat mood disorders. In another embodiment, a system in accordance with the present invention is used to treat persistent negative moods by enhancing a person's mood. The system may take the form of a social networking website or a stand-alone application. In an embodiment, the system uses a social networking website to assist users in performing the actions and having the experiences necessary to adjust the structure or chemistry of their brains.

In an illustrative embodiment where the system includes a social media website as described above, a user may be diagnosed with a mood disorder by a medical professional, such as a physician. Alternatively, a user may self-diagnose based on observed symptoms. Once a user has been diagnosed with a mood disorder, the user creates an account on the social networking website and enters information into his or her profile page. The user then uses the features of the website to measure his or her mood and track his or her mood over time. By measuring a user's mood, the website is able to indirectly monitor the user's neurological structure and neurochemistry. By completing exercises such as challenges on the website and interacting with other users, the user may alter his or her neurological structure or neurochemistry (that is, the ratio of neurotransmitters) in his or her brain, thereby offering relief from the symptoms of the mood disorder. By sufficiently modifying the user's neurological structure or neurochemistry, the user may be effectively "cured" of the symptoms of the mood disorder. However, even a user that does not have a diagnosed mood disorder may use the social networking website to ensure the user maintains a healthier brain and to assist other users in similarly treating their conditions.

Endorphins and Euphoria

Endorphins are hormones that function as inhibitory neurotransmitters that are naturally produced in the human body by the pituitary gland and hypothalamus. Endorphins produce feelings of relaxation, happiness, and well-being in a person. Further, endorphins have an analgesic effect by inhibiting receptors in the brain that receive pain messages. Research has established that endorphins are produced from a variety of activities, including exercise and meditation. Psychological triggers, such as positive thinking or reflecting on pleasurable things such as happy events in a person's life, may also trigger the release of endorphins. Additional positive effects, such as improved sleep, lower blood pressure and cholesterol, and reduced levels of stress may also result from increased endorphin levels.

In an embodiment of the present invention, the system promotes feelings of relaxation, happiness, and well-being in a person by promoting positive thought. For example, by reflecting on five events that occurred that day that made a person happy, he or she can trigger the release of endorphins and produce a sensation of euphoria. Similarly, by repeatedly practicing positive thinking, a person may change the neurological response of his or her body so that endorphins are released more easily or more frequently. In an embodiment, the system works to change a person's neurochemistry or the chemistry of a person's blood to naturally include increased endorphin levels. In an embodiment, the increased endorphin levels are sufficient to produce a feeling of euphoria.

It is understood that the preceding is merely a detailed description of some examples and embodiments of the present invention and that numerous changes to the disclosed embodiments can be made in accordance with the disclosure made herein without departing from the spirit or scope of the invention. The preceding description, therefore, is not meant to limit the scope of the invention but to provide sufficient disclosure to one of ordinary skill in the art to practice the invention without undue burden.

What is claimed is:

1. A system for modifying a user's neurological structure or neurochemistry by improving at least one attribute of the user, wherein the at least one attribute is selected from the group comprising a mood, a positivity level, and a resilience level, the system comprising a processor, a non-transitory memory, a display, and an input device, the memory containing a program, wherein said program is configured to call the processor to execute the steps of:

presenting the user with a user interface providing at least one task associated with positive behavior via the display;

adapting the user interface based on an input from the user to allow the user to complete one or more of the at least one task associated with positive behavior via the input device;

determining whether the user completed one or more of the at least one task associated with positive behavior;

tracking a number of tasks associated with positive behavior completed by the user;

displaying, with the user interface via the display, a first indicium which is representative of the number of tasks associated with positive behavior completed by the user;

adapting the user interface to present the user with at least one action via the display, wherein the at least one action is determined based in part on the number of tasks associated with positive behavior completed by the user;

measuring the at least one attribute of the user at a plurality of times using one or more of a plurality of tests, wherein the one or more of the plurality of tests are displayed to the user via the display device and require the user to provide an input using the input device;

tracking the at least one attribute of the user at the plurality of times by recording one or more results of the one or more of the plurality of tests;

displaying, with the user interface via the display, a second indicium which is representative of the at least one attribute of the user at the plurality of times;

alerting the user via the display to one or more of a plurality of factors that may affect the at least one attribute of the user based on the one or more results of the one or more of the plurality of tests;

modifying the user's neurological structure or neurochemistry by improving the at least one attribute of the user so as to provide cognitive benefits to the user.

2. The system of claim 1, further defined as a system for treating a mood disorder of the user diagnosed by a medical expert, the user having refused to use medication to treat the user's disorder due to personal, emotional, or spiritual beliefs, the processor further executing the steps of:

modifying the user's neurological structure or neurochemistry so as to relieve the symptoms of the mood disorder.

3. The system of claim 1, further defined as a system for inducing a positive mood in a user, the processor further executing the steps of:

modifying the user's neurological structure or neurochemistry so as induce a state of euphoria in the user.

4. The system of claim 1, wherein the processor further executes the steps of:

adapting the user interface to present the user via the display with a listing containing a plurality of other users of the system;

receiving, from the user via the input device, a second input representative of at least one of the plurality of other users of the system;

adapting the user interface to present the user via the display with a plurality of actions designed to positively affect the neurological structure or neurochemistry of the plurality of other users of the system represented by the second input via at least one characteristic of the at least one of the plurality of other users of the system represented by the second input, wherein the characteristic is selected from the group comprising a mood, a positivity level, and a resilience level;

receiving, from the user via the input device, a third input representative of at least one of the plurality of actions; and performing the at least one of the plurality of actions represented by the third input.

5. The system of claim 1, wherein the processor further executes the steps of:

adapting the user interface to present the user via the display with a listing containing a plurality of tools designed to positively affect the user's neurological structure or neurochemistry via the at least one attribute of the user;

receiving, from the user via the input device, a second input representative of at least one of the plurality of tools;

adapting the user interface to present to the user via the display with the at least one tool represented by the second input;

using the at least one tool represented by the second input to positively affect the user's neurological structure or neurochemistry by positively affecting the at least one attribute of the user.

6. The system of claim 1, wherein the processor further executes the steps of:

adapting the user interface to present to the user via the display with a tool designed to positively impact the at least one attribute of the user, wherein the tool is selected based on the at least one attribute of the user at the time.

7. The system of claim 1, wherein the processor is a first processor, the memory is a first memory, the input device is a first input device and the system further comprises:

a portable device comprising a second processor communicatively coupled to the first processor, a second memory, and a second input device, the second processor operating a second program stored in the second memory by executing the steps of:

receiving a second input via the second input device;

providing the first processor with a signal indicating the user has completed one or more of the at least one task associated with positive behavior based on the second input.

8. The system of claim 7, wherein the portable device further comprises a second display and the second processor further executes the steps of:

displaying, via the second display, the indicium representing the number of tasks associated with positive behavior completed by the user.

9. A system for modifying a user's neurological structure or neurochemistry by improving at least one attribute of the user, wherein the at least one attribute is selected from the group comprising a mood, a positivity level, and a resilience level, the system comprising:
  at least a host computer comprising
    a central processing unit (CPU) for executing a software comprising a plurality of instructions,
    a non-transitory memory communicatively connected to the CPU containing the software;
    a display device communicatively connected to the CPU, and
    an input device communicatively coupled to the CPU, wherein the CPU is configured to execute the plurality of instructions which implement:
      a task generation module that generates a plurality of tasks designed to alter the neurochemistry or neurological structure of the user, displays the plurality of tasks to the user via the display device, receives a first input from the user via the input device indicating at least one selected task from the plurality of tasks, and allows the user to complete the at least one selected task via the display device and the input device;
      a progress recordation module that records the progress of the user in completing the plurality of tasks and displays the progress of the user in completing the plurality of tasks to the user via the display device;
      a reward module that generates a plurality of actions, displays the plurality of actions to the user via the display device, receives a second input from the user via the input device indicating at least one selected action from the plurality of actions, and allows the user to perform the at least one selected action via the display device and the input device, wherein the plurality of actions is determined based on the progress of the user in completing the plurality of tasks;
      a measurement module that measures the at least one attribute of the user, displays a plurality of tests to the user via the display device, receives a third input from the user via the input device indicating at least one selected test from the plurality of tests, and administers the at least one selected test to the user via the display device and the input device;
      a recordation module that records the at least one attribute of the user based on the results of the at least one selected test and displays an indication of the at least one attribute of the user to the user via the display device; and
      a recommendation module that generates at least one recommendation for the user and displays the at least one recommendation to the user via the display device, wherein the at least one recommendation is based at least in part on the at least one attribute of the user, lists at least one factor that may affect the at least one attribute of the user, and is designed to assist the user in positively altering the user's neurochemistry or neurological structure,
  wherein the system further comprises a portable device comprising a processor communicatively coupled to the CPU, a second memory containing a second software comprising a second plurality of instructions, and a second input device, wherein the processor of the portable device is configured to execute the second plurality of instructions which implement:
    a portable input module that receives a fourth input via the second input device; and
    a communication module that provides the CPU with a signal indicating the user has completed one or more of the at least one task associated with positive behavior based on the fourth input.

10. The system of claim 9, further defined as a system for relieving the symptoms of a mood disorder of the user diagnosed by a medical expert, the software further comprising:
  a relief module for modifying the user's neurological structure or neurochemistry so as to relieve the symptoms of the mood disorder.

11. The system of claim 9, further defined as a system for inducing a positive mood in a user, the software further comprising:
  a mood improvement module for modifying the user's neurological structure or neurochemistry so as induce a state euphoria or inner well-being in the user.

12. The system of claim 9, wherein the software further comprises a message module that:
  generates a listing containing a plurality of other users of the system;
  displays the listing to the user via the display device;
  receives, from the user via the second input device, a fifth input representative of at least one of the plurality of other users of the system;
  determines a plurality of actions designed to positively affect the neurological structure or neurochemistry of the at least one of the plurality of other users by positively affecting at least one characteristic of the at least one of the plurality of other users of the system represented by the fifth input, wherein the characteristic is selected from the group comprising a mood, a positivity level, and a resilience level;
  displays the plurality of actions to the user via the display device;
  receives, from the user via the input device, a sixth input representative of at least one of the plurality of actions; and
  performs the at least one of the plurality of actions represented by the sixth input.

13. The system of claim 9, wherein the software further comprises a module for positively affecting the at least one attribute of the user that:
  generates a listing containing a plurality of tools designed to positively affect the at least one attribute of the user;
  displays the listing to the user via the display device;
  receives, from the user via the second input device, a fifth input representative of at least one of the plurality of tools;
  displays to the user via the display the at least one tool represented by the fifth input; and
  positively affects the neurochemistry or neurological structure of the user by using the at least one tool represented by the second input to positively affect the at least one attribute of the user.

14. The system of claim 9, wherein the software further comprises a module for positively affecting the at least one attribute of the user at a particular time that:
  displays a tool designed to positively impact the neurochemistry or neurological structure of the user by positively impacting the last least one attribute of the user to the user via the display device, wherein the tool is selected based on the at least one attribute of the user at the time.

15. The system of claim 9, wherein the portable device further comprises a second display device and the second software further comprises:

a visualization module that displays, via the second display device, the indicium representing the number of tasks associated with positive behavior completed by the user.

* * * * *